United States Patent
Yoshitome

(10) Patent No.: US 7,669,490 B2
(45) Date of Patent: Mar. 2, 2010

(54) APPARATUS AND METHOD FOR TESTING FILTERS IN A CLEAN ROOM

(75) Inventor: Yasuhiro Yoshitome, Hirakata (JP)

(73) Assignee: Taikisha Ltd., Tokyo (JP)

( * ) Notice: Subject to any disclaimer, the term of this patent is extended or adjusted under 35 U.S.C. 154(b) by 357 days.

(21) Appl. No.: 11/661,246

(22) PCT Filed: May 11, 2005

(86) PCT No.: PCT/JP2005/008614

§ 371 (c)(1),
(2), (4) Date: Feb. 26, 2007

(87) PCT Pub. No.: WO2006/022051

PCT Pub. Date: Mar. 2, 2006

(65) Prior Publication Data

US 2008/0210000 A1    Sep. 4, 2008

(30) Foreign Application Priority Data

Aug. 27, 2004  (JP) .............................. 2004-248108

(51) Int. Cl.
*G01M 19/00* (2006.01)
*G01M 3/20* (2006.01)
*B01D 65/10* (2006.01)

(52) U.S. Cl. .................... 73/865.8; 73/31.02; 73/31.03; 210/85; 210/87

(58) Field of Classification Search ................ 73/31.01, 73/31.02, 31.03, 865.8; 210/85, 87, 93
See application file for complete search history.

(56) References Cited

U.S. PATENT DOCUMENTS 4,494,403 A * 1/1985 Bowers et al. ............... 73/40.7
4,765,810 A * 8/1988 Wetzel ........................ 96/417
4,862,047 A   8/1989 Suzuki et al.
4,924,153 A   5/1990 Toru et al.
5,097,604 A * 3/1992 Brown ......................... 33/613
6,033,301 A * 3/2000 Suwa ......................... 454/187
6,755,734 B2 * 6/2004 Yokoyama et al. .......... 454/187

FOREIGN PATENT DOCUMENTS

DE           4041588 A1 *  6/1992
JP           59-010831      1/1984
JP           59010831 A *   1/1984

(Continued)

*Primary Examiner*—David A. Rogers
(74) *Attorney, Agent, or Firm*—The Webb Law Firm

(57) ABSTRACT

To provide a filter test apparatus that can easily and efficiently test parallel filters in a clean room, a plurality of filters for purifying air supplied into the room are disposed in parallel, and a moving frame oriented along the exit surfaces of a filter group is disposed in the clean room, in which the exit surfaces of the filter group are used as the ceiling surfaces or side surfaces of the room, so as to allow movement in the direction along the exit surfaces of the filter group in a direction orthogonal to the longitudinal direction of the moving frame. The moving frame is disposed so as to span opposing room walls and in a position near the exit surfaces of the filter group in the room. A filter test device is movably mounted on the moving frame in the longitudinal direction of the moving frame.

8 Claims, 15 Drawing Sheets

FOREIGN PATENT DOCUMENTS

| | | |
|---|---|---|
| JP | 60-210720 | 10/1985 |
| JP | 63111509 A * | 5/1988 |
| JP | 02129533 A * | 5/1990 |
| JP | 2-048771 Y2 | 12/1990 |
| JP | 09010534 A * | 1/1997 |
| JP | 63-7820 | 1/1998 |
| JP | 11-014532 A | 1/1999 |
| JP | 3283440 | 1/1999 |
| JP | 2001108606 A * | 4/2001 |
| JP | 2001-241717 | 9/2001 |
| JP | 2002221482 A * | 8/2002 |
| JP | 2004-157038 | 6/2004 |

* cited by examiner

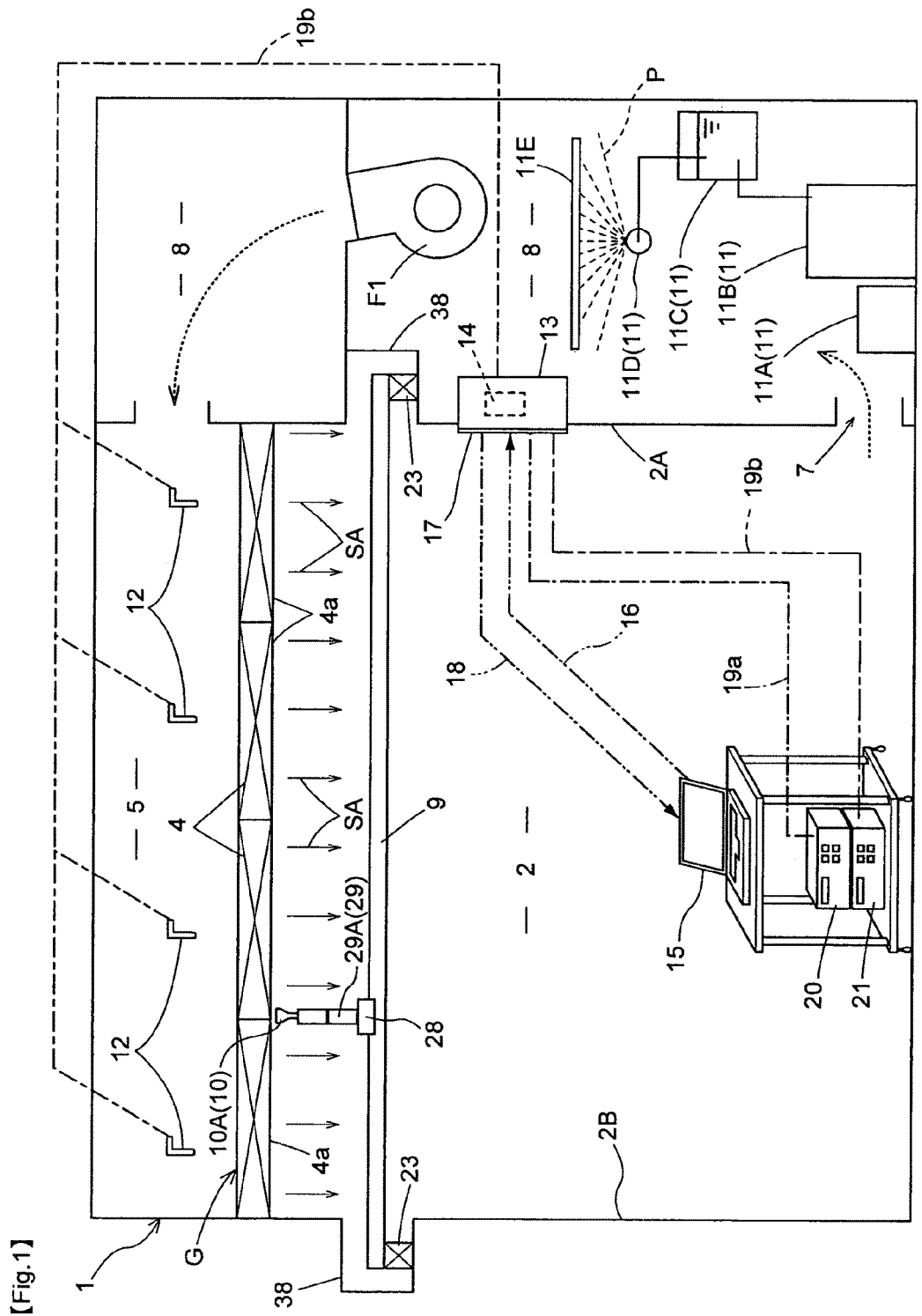
[Fig.1]

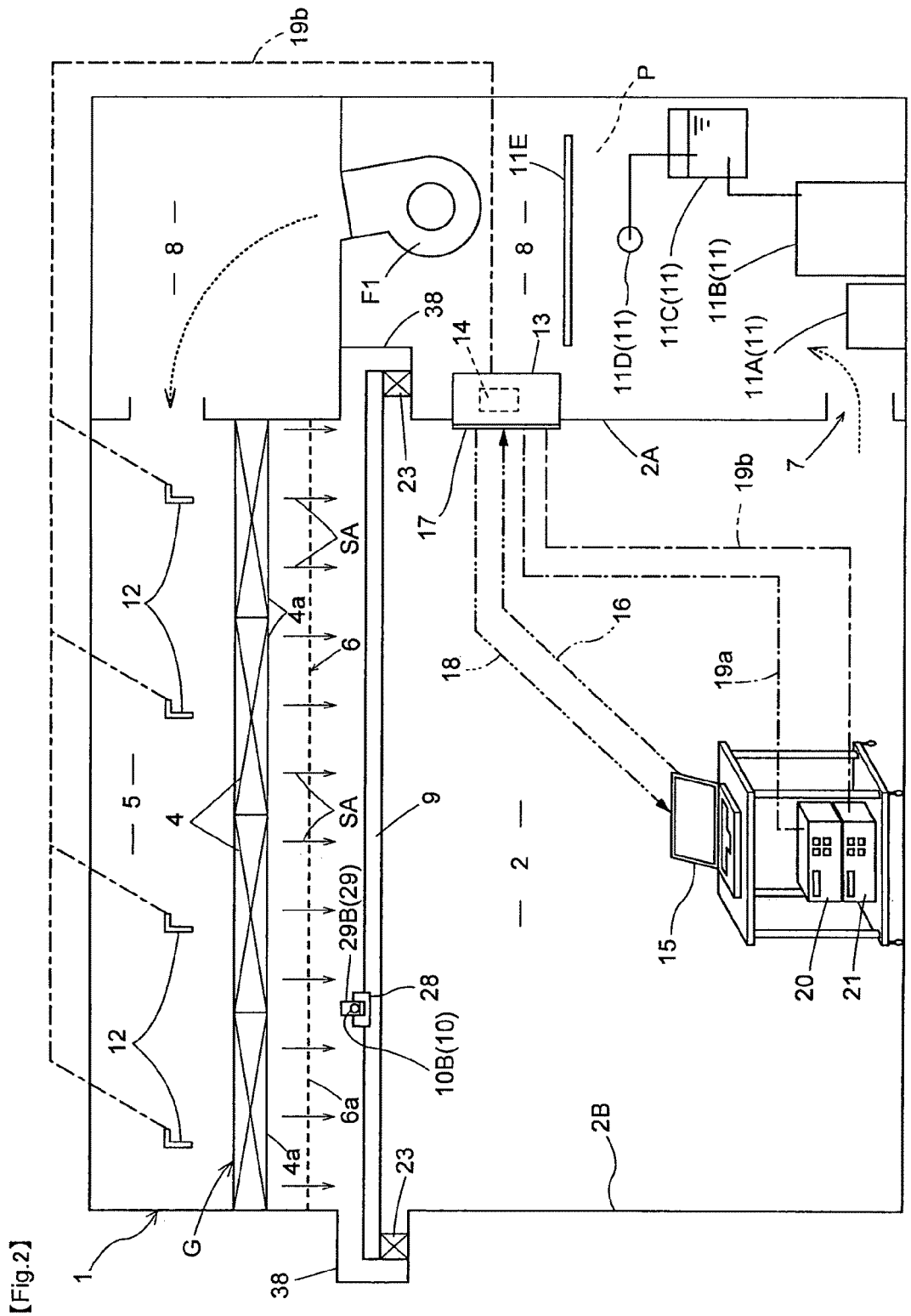
[Fig.2]

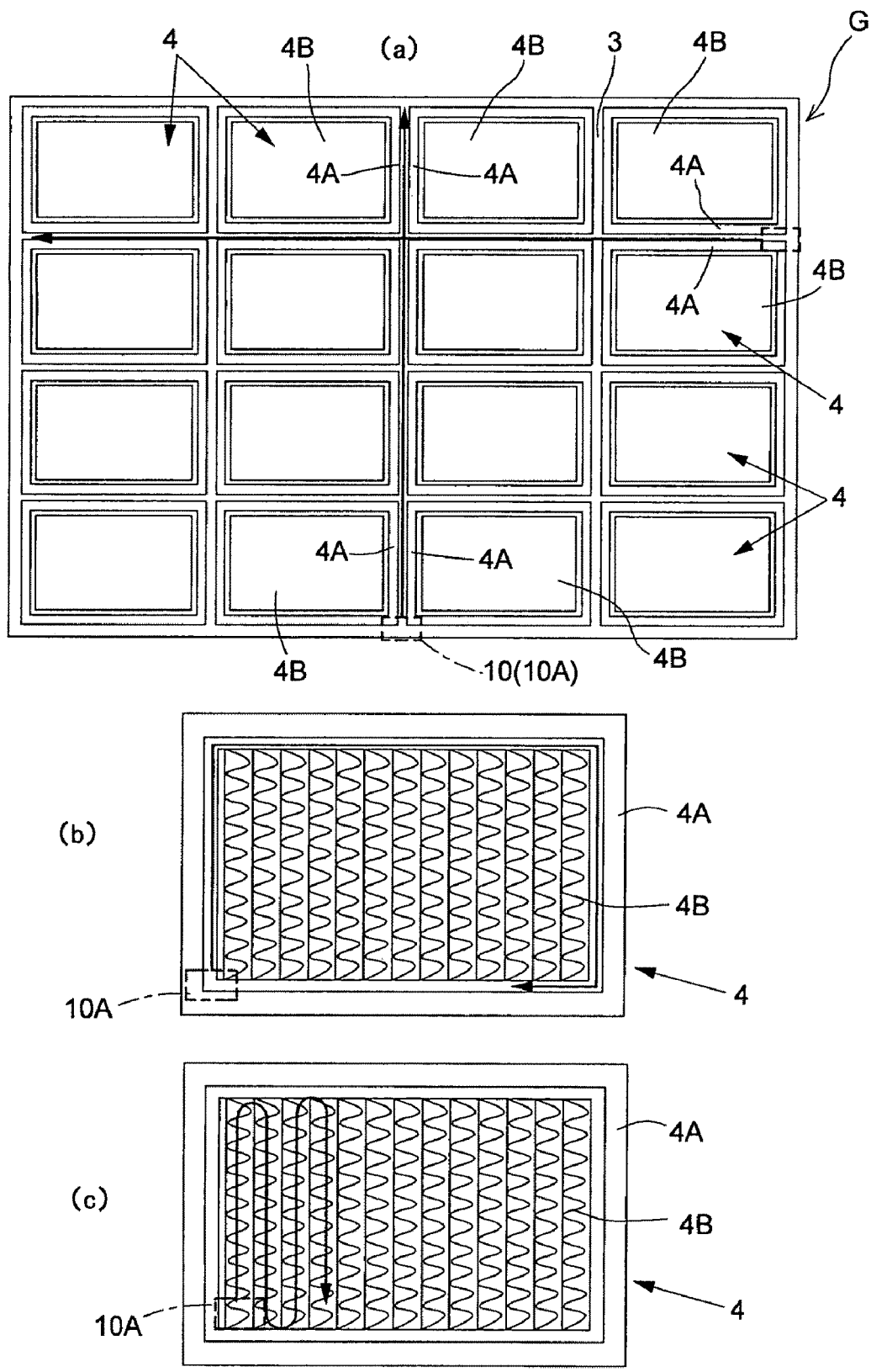
[Fig.3]

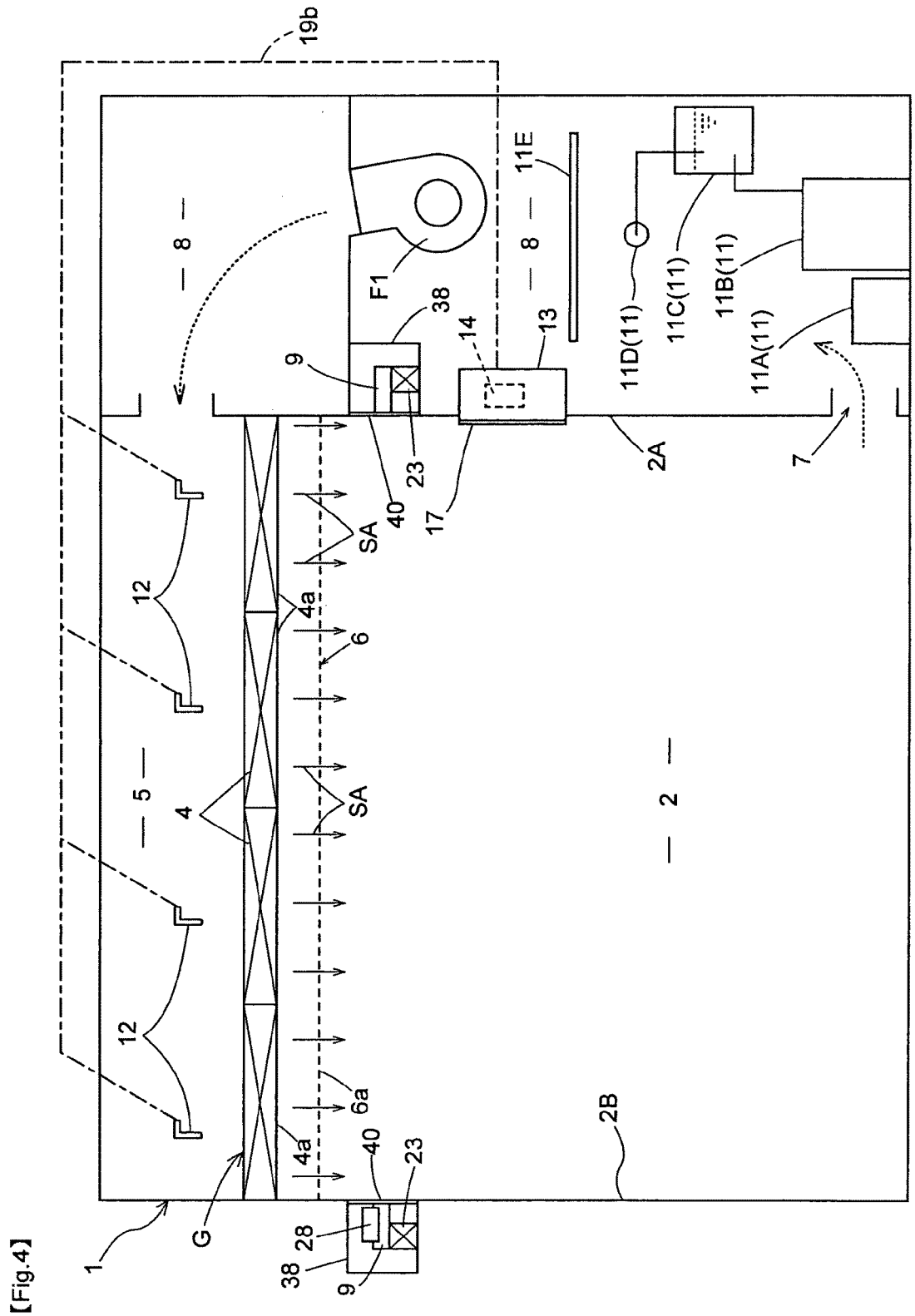
[Fig.4]

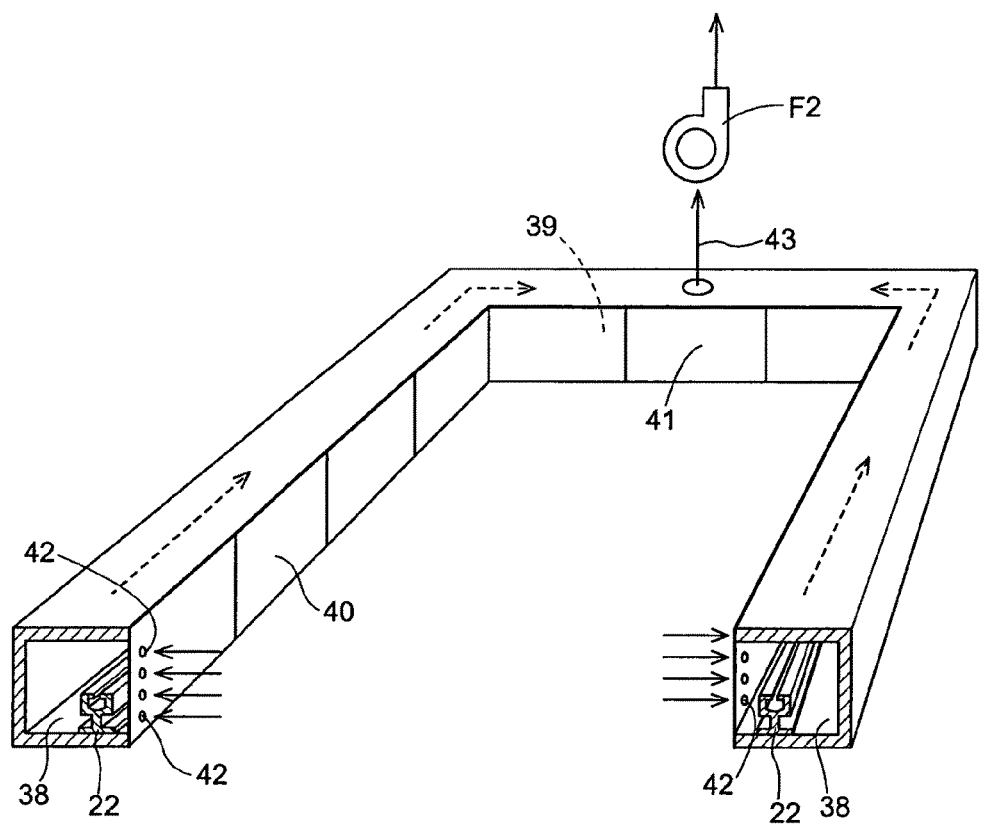
[Fig.5]

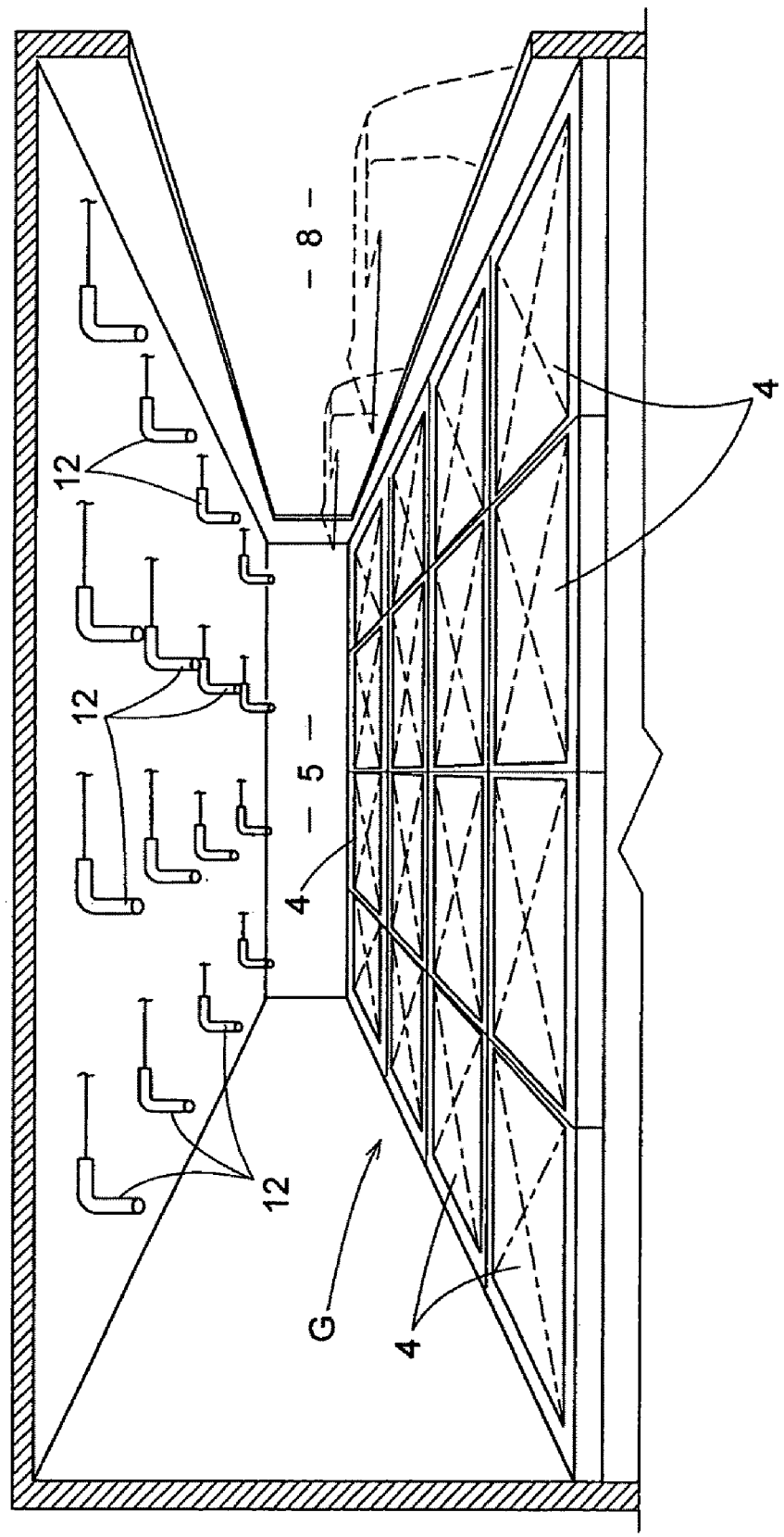
[Fig.6]

[Fig.7]
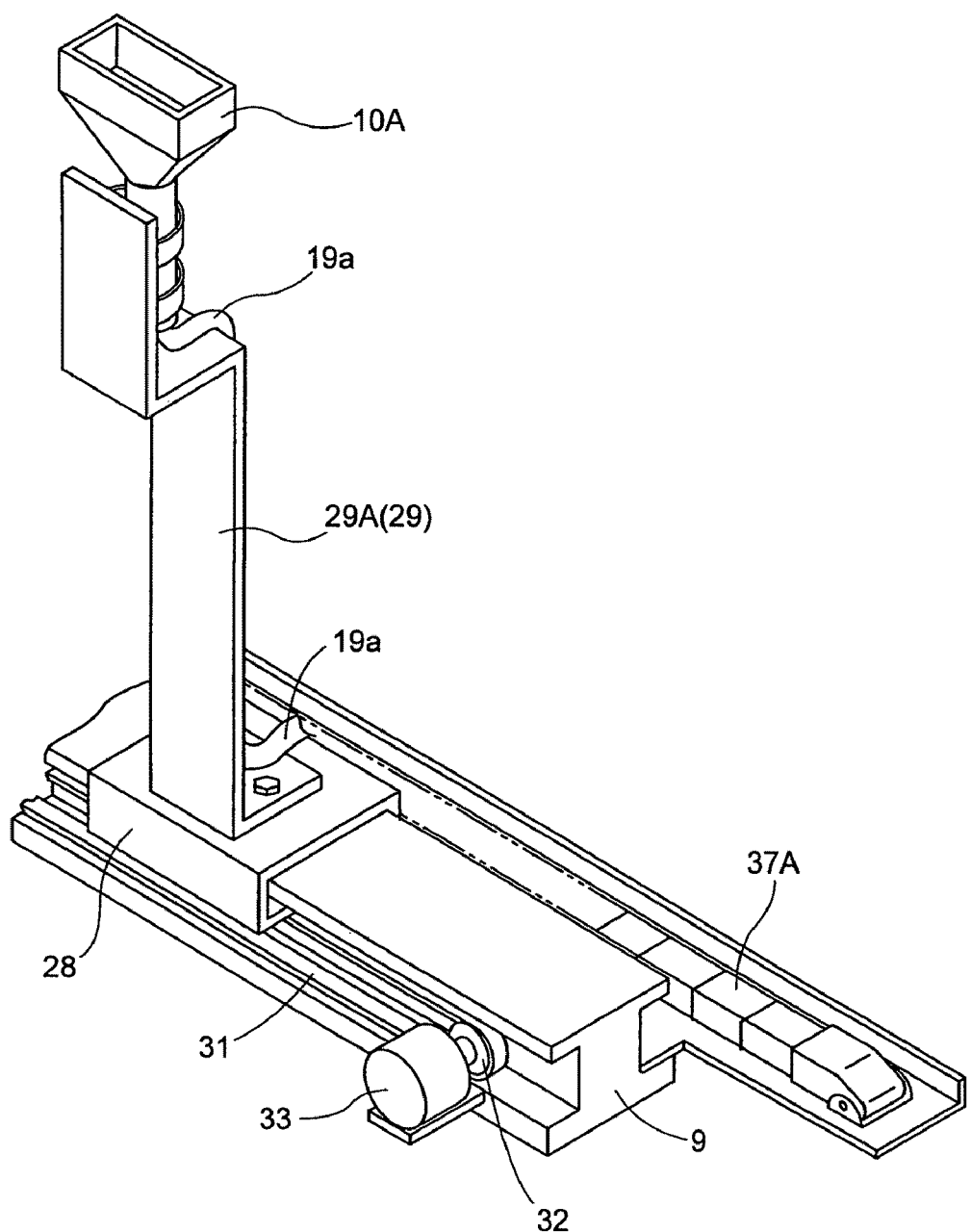

[Fig.8]
(a)
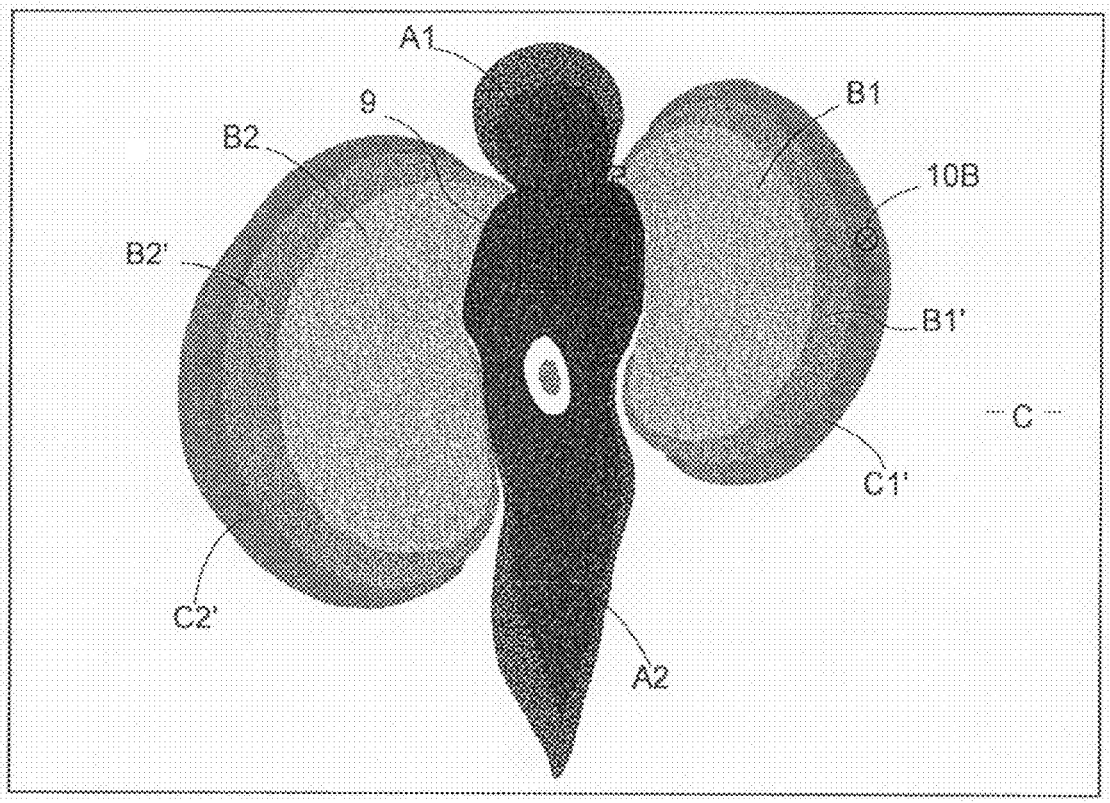
(b)
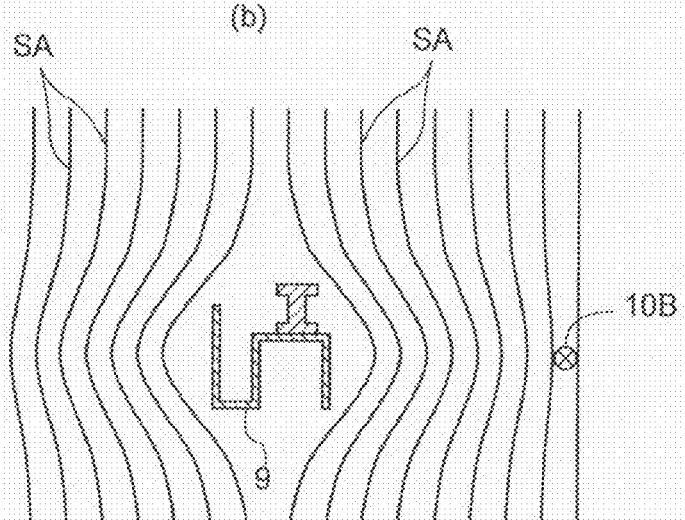

[Fig.9]
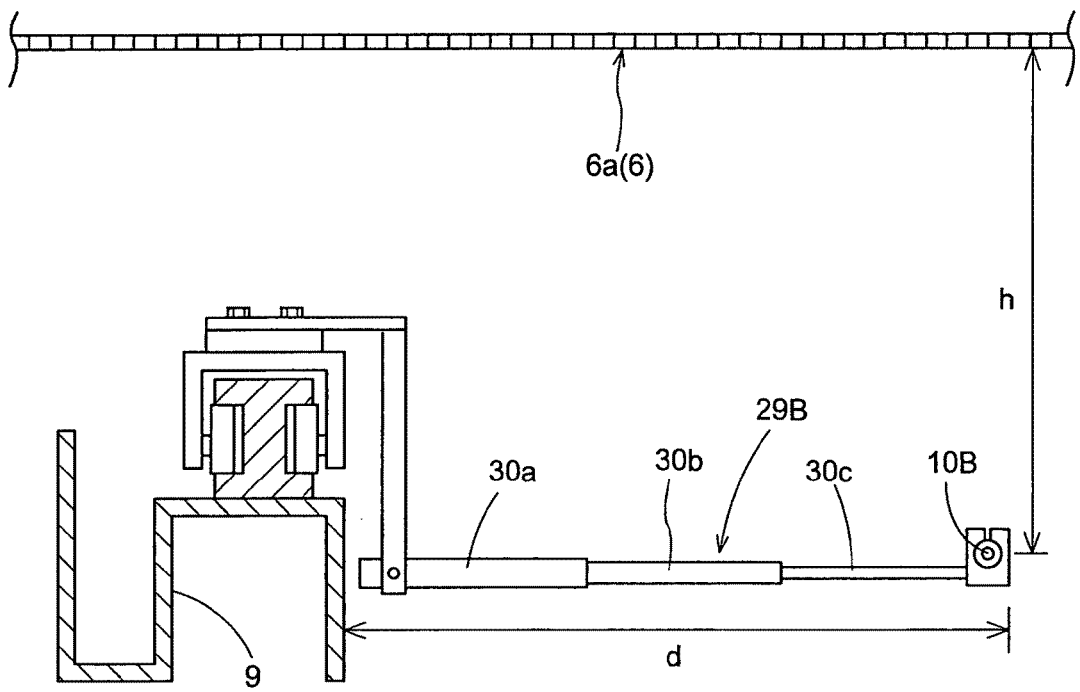
[Fig.10]
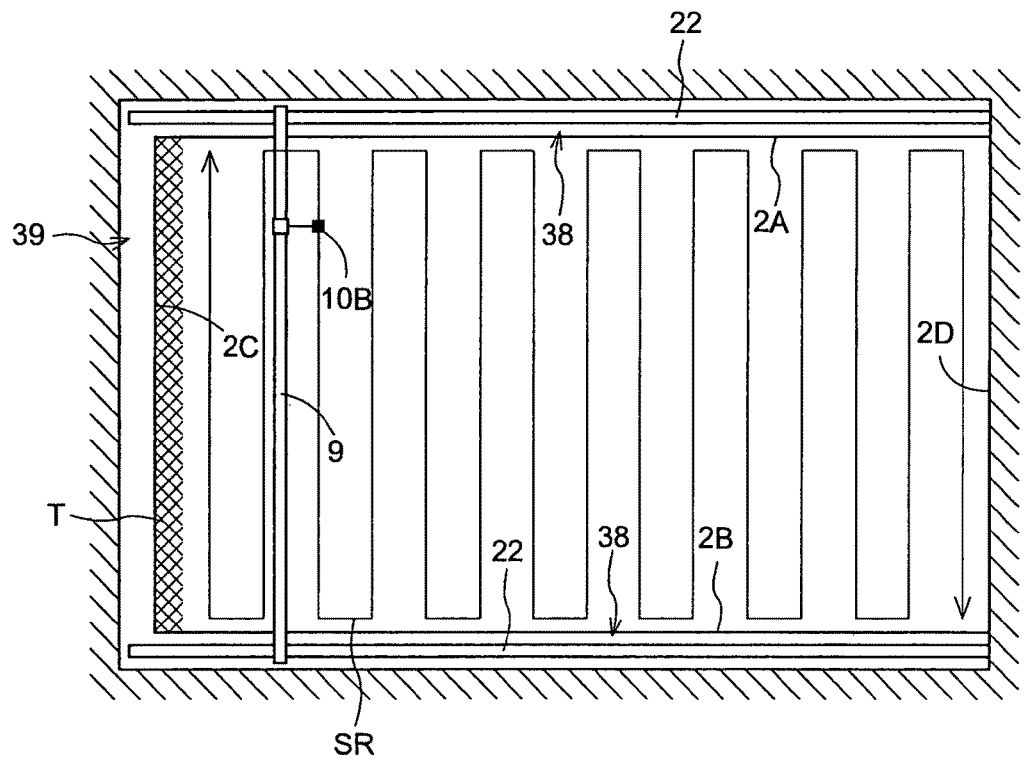

[Fig.11]
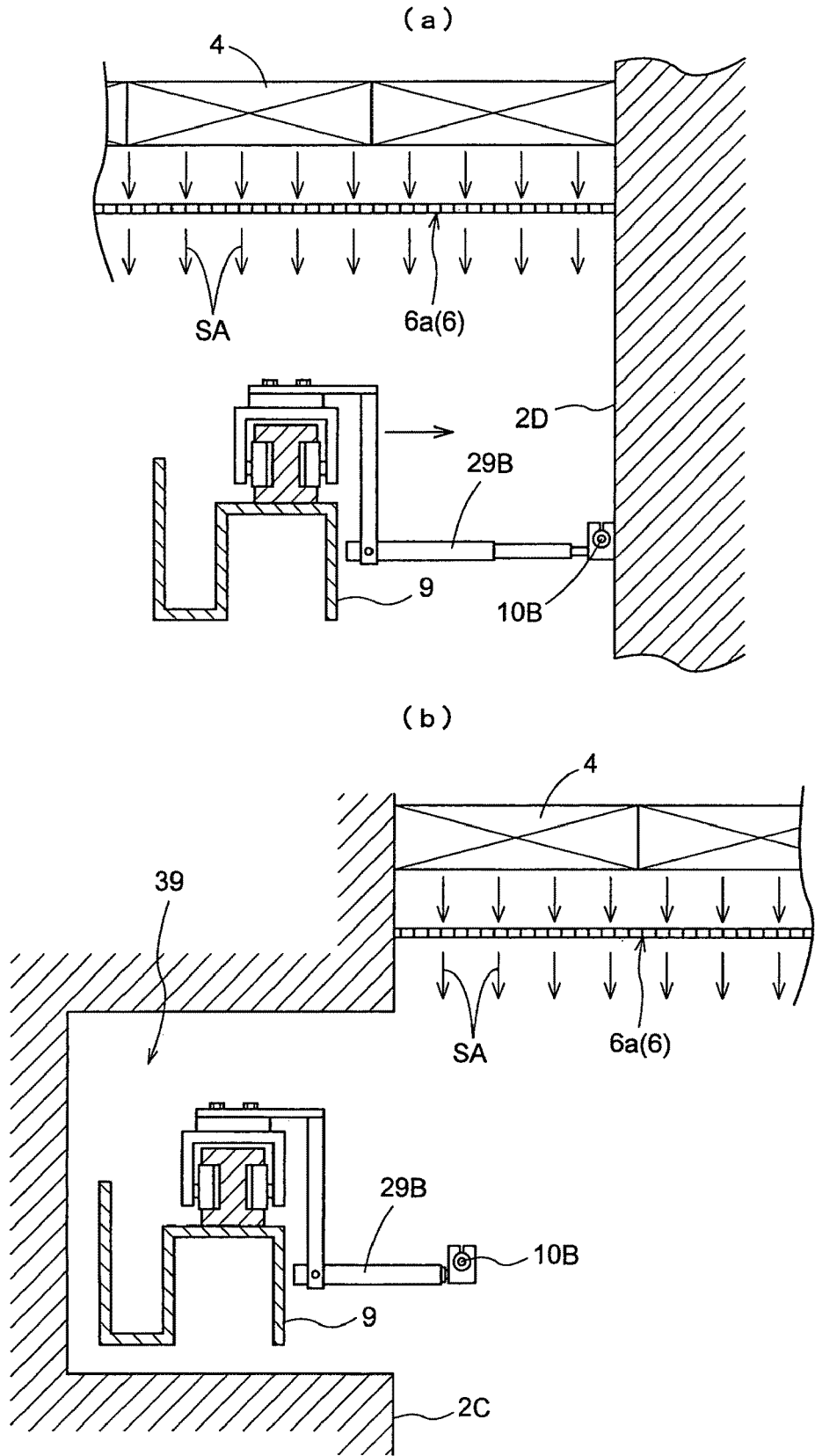

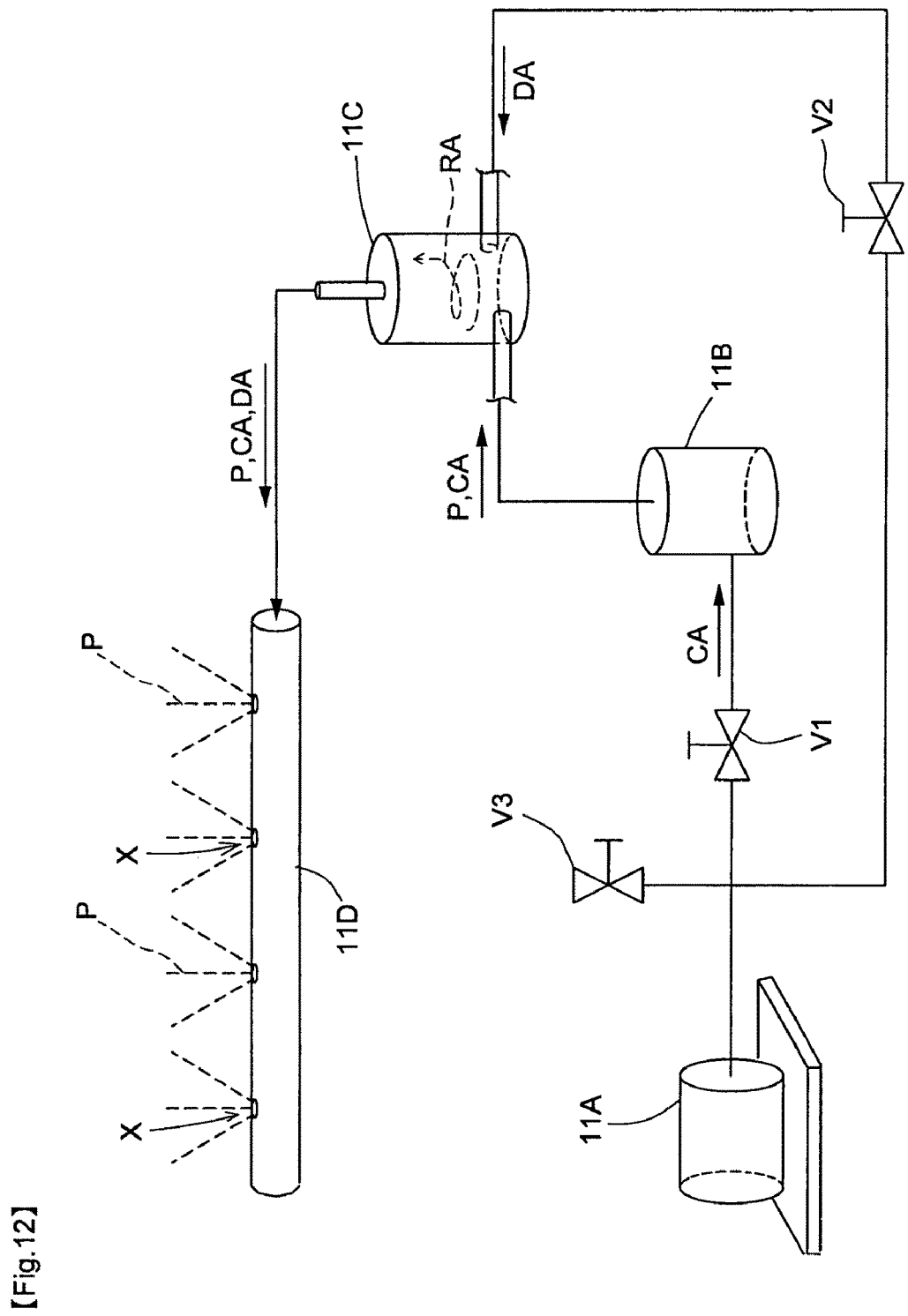
[Fig.12]

[Fig. 13]
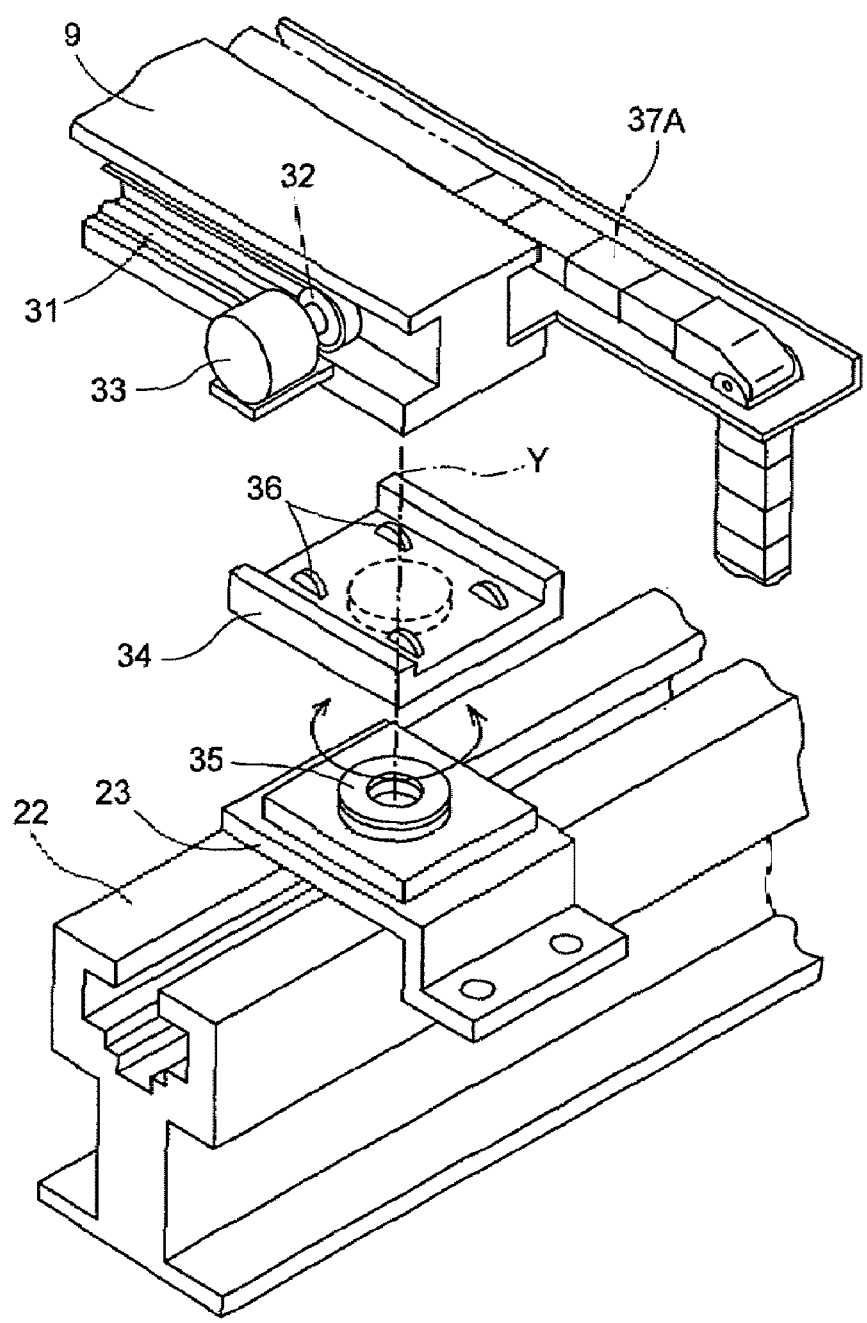

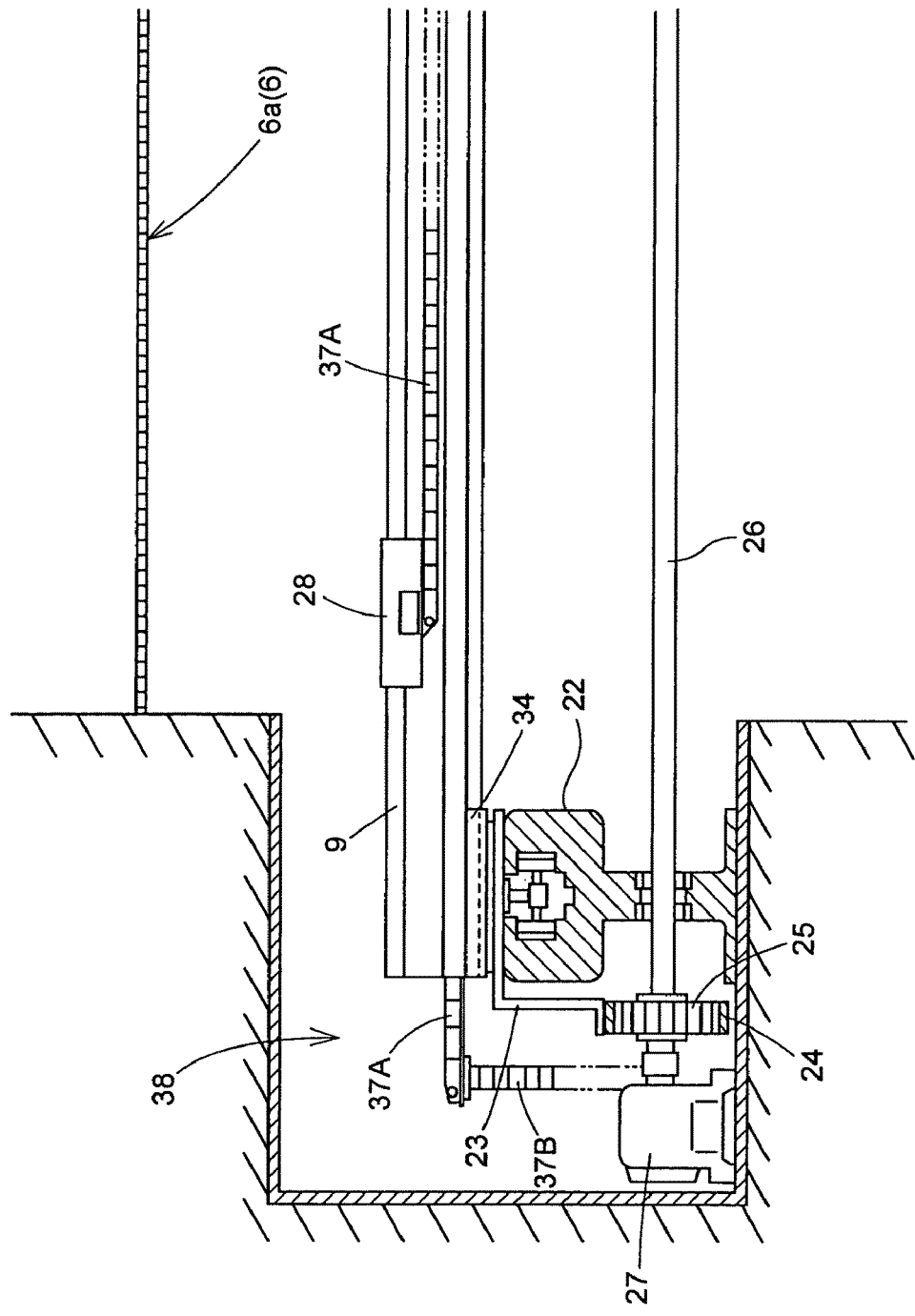
[Fig.14]

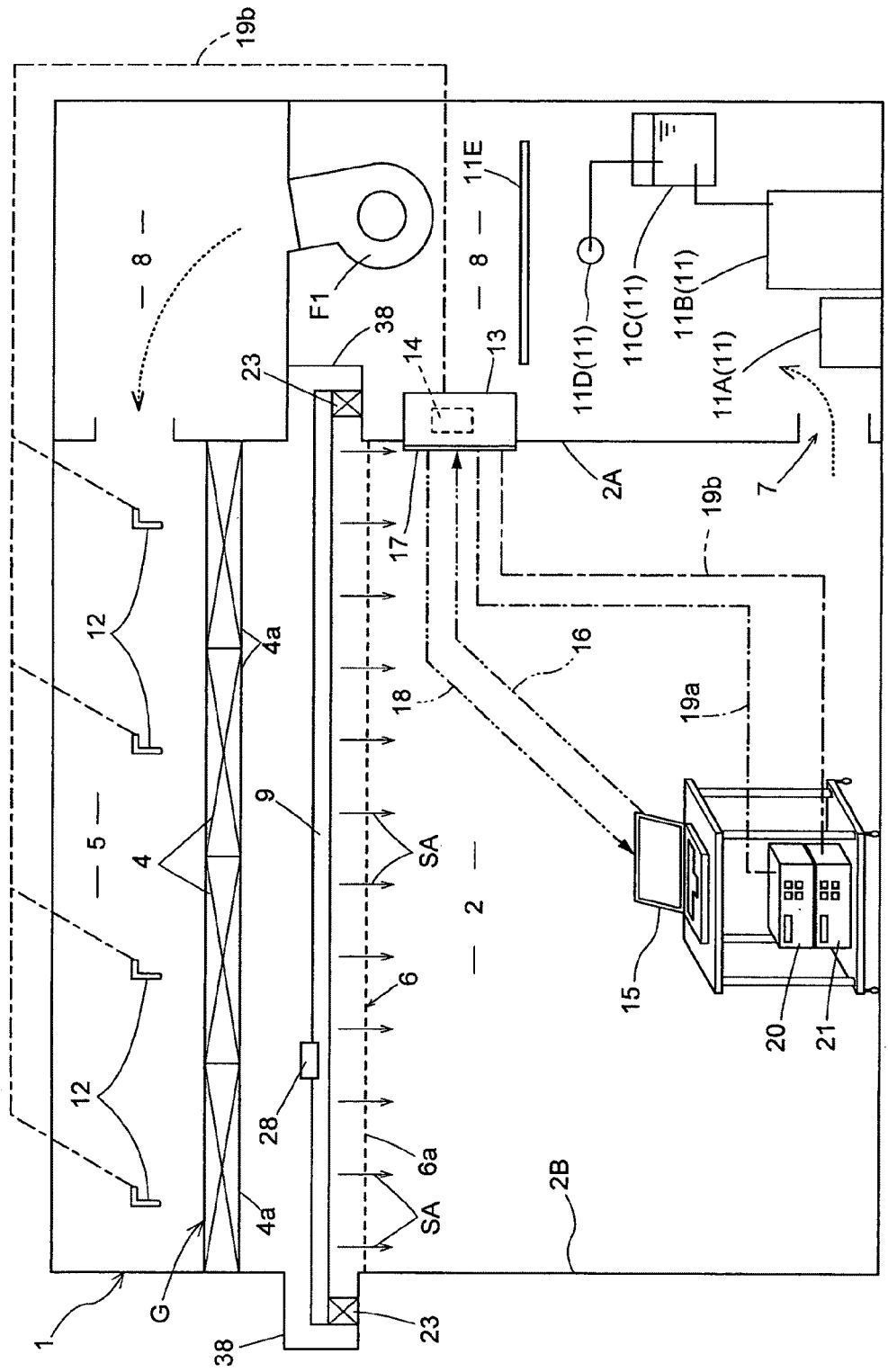
[Fig.15]

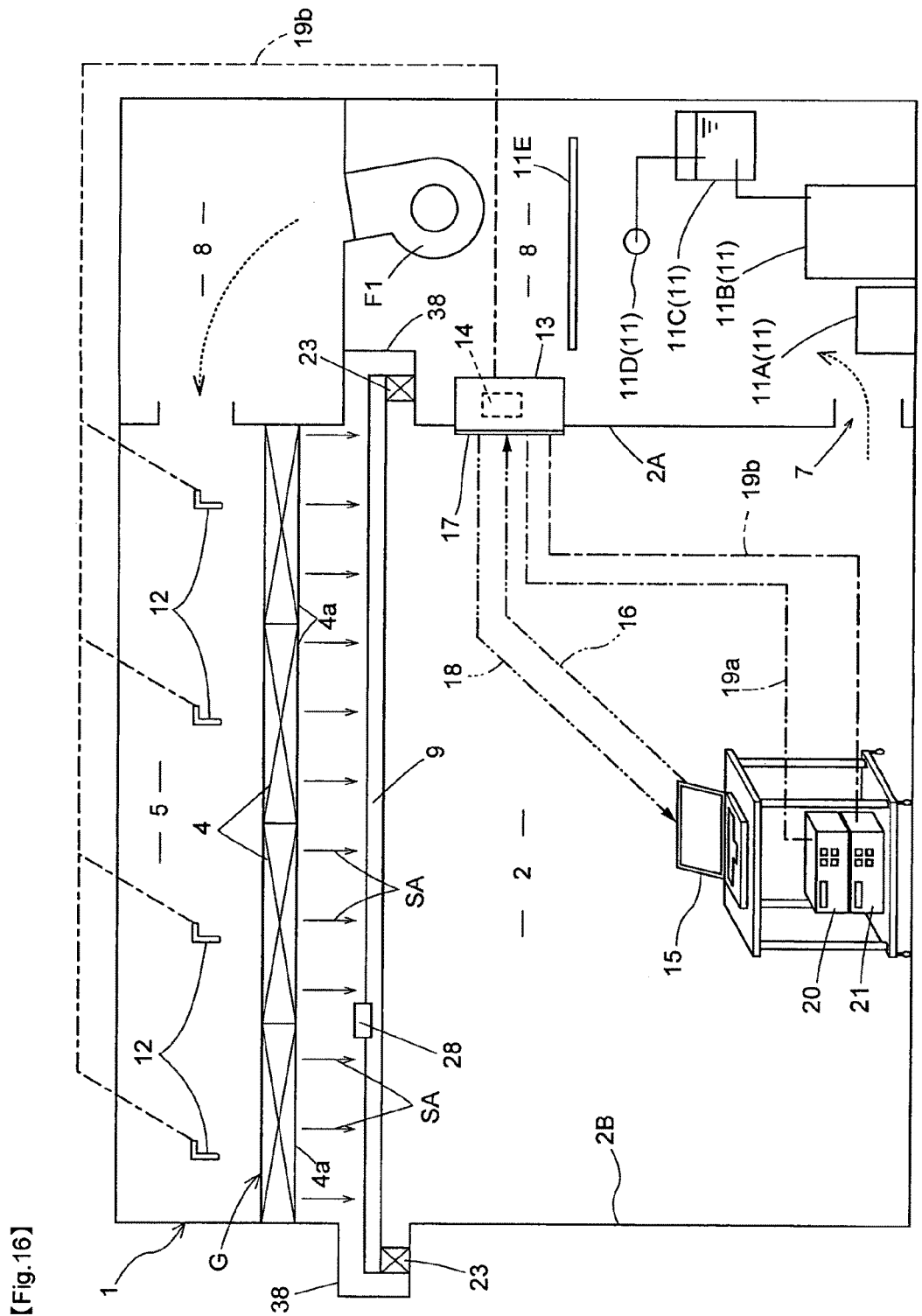
[Fig. 16]

APPARATUS AND METHOD FOR TESTING FILTERS IN A CLEAN ROOM

TECHNICAL FIELD

The present invention relates to a filter testing apparatus, and specifically to a filter testing apparatus adapted for use in a clean room provided with a plurality of filters arranged in parallel for purifying air supplied to the room, a ceiling surface or a side surface of the room acting as exit surfaces of a group of the filters for carrying out leak testing, air discharge velocity testing and other types of testing of the filters in the clean room.

BACKGROUND ART

Conventionally, a scanner for moving a filter test device in XY directions to perform scanning is mounted on a filter support frame on both sides of a single filter so as to straddle the filter. When so mounted, the filter test device scans the exit surface of the straddled filter (e.g., see Patent Document 1).

There are also devices in which a scanner movable in the XY directions or provided with a movable arm is placed on a cart that travels on the floor, and a filter test device is used to scan the exit surface of filters above the cart using the scanner mounted on the cart (refer, e.g., Patent Document 2 and Patent Document 3).

Patent Document 1: Japanese Patent Publication No. 3-50210
Patent Document 2: Japanese Patent Publication No. 5-10605
Patent Document 3: Japanese Laid-open Patent Application No. 63-7820

DISCLOSURE OF THE INVENTION

Problems to be Solved by the Invention

In either type of conventional apparatus, the filter test device is moved by the scanner to perform scanning in order to test all of the filters in a clean room. In addition, the test apparatus itself (i.e., the entire test apparatus) must be sequentially moved to positions that correspond to the filters to be tested by moving the cart or switching the scanner on the filter support frame. For this reason, the test work is laborious and inefficient.

In particular, in case of a clean room in which the exit surfaces of a filter group act as a ceiling surface, installed equipment in the room must often be moved to another location, because the cart travels throughout the entire room and scanner remounting work on the filter support frame is done throughout the entire room also. Therefore, the test work becomes even more laborious and less efficient.

In view of the foregoing, a primary object of the present invention is to provide a filter testing apparatus that solves the above-described problems and that can easily improve efficiency of testing the filters in a clean room by increasing efficiency of the movement of a filter test device when the filters are tested in the clean room.

Means for Solving the Problems

[1] The first aspect of the present invention is related to a filter testing apparatus adapted for use in a clean room provided with a plurality of filters arranged in parallel for purifying air supplied to the room, a ceiling surface or a side surface of the room acting as exit surfaces of a group of the filters, the apparatus comprising:

a moving frame oriented along the exit surfaces of the filter group to be movable in a direction along the exit surface orthogonal to the longitudinal direction thereof, and spanned by opposite walls of the room in a position of the room near the exit surfaces; and a filter test device movably mounted on the moving frame in the longitudinal direction of the moving frame.

With this configuration, a filter test device can easily be moved to any location on the exit surface of the filter group by merely combining the movement of a moving frame disposed across the room walls and the movement of a filter test device in relation to the moving frame. Also, the filter test device can be caused to continuously scan/move across the entire surface of the exit surfaces of the filter group.

In other words, all of the filters in the clean room can be tested without the need to replace the scanner on the filter support frame or sequentially move the test apparatus itself by e.g. moving a cart.

The moving frame is disposed across the room walls at positions near the exit surfaces of the filter group, to move it in directions along the exit surfaces. Therefore, even when the clean room has the exit surfaces of the filters disposed in the ceiling, the scanner does not need remounting on the filter support frame as described above, or traveling a cart and other operations. Additionally, the filters can be tested without the need to remove equipment installed in the room to another location in order to allow the moving frame to move, and the amount of room installed equipment that must be moved can be considerably reduced. In view of the above, the filters in the clean room can be much more easily tested and testing efficiency can be considerably increased.

Also, when leaks through the inter-frame seals of adjacent filters (the sealing portion between the filter frames of adjacent filters) are to be tested using a conventional apparatus in which the test apparatus itself is sequentially moved to positions that correspond to the filters being tested, redundant leak testing occurs between the leak test of an inter-frame seal is the area around a filter, and the subsequent leak test of an inter-frame seal in the area around an adjacent filter when the testing device has moved to the next position. Scanning control becomes more difficult because various modifications must be made to the scanning route to avoid redundant testing when the scanner scans/moves the filter test device. As described above, in accordance with the first aspect of the present invention, the inter-frame sealing portion that linearly connects a plurality of filters at the exit surfaces of the filter group can be tested for leaks continuously from one end to the other end and redundant leak testing can be eliminated as described above, because there is no need to sequentially move the test apparatus itself and the filter test device can be moved to any location of the exit surfaces of the filter group. In view of the above, the ease and efficiency of testing the filters in a clean room can be enhanced.

In implementing the first aspect of the present invention, the specific details of tests in which supplied air is discharged from the exit surfaces of a filter group may be an air velocity test that involves supplied air discharged from the exit surfaces of the filter group, a purity test that involves purified air discharged from the exit surfaces of the filter group (i.e., a leak test of the filter group), a temperature/humidity test that involves supplied air that has passed through the filter group, or any other test as long as a filter test device mounted on a moving frame is used to carry out the testing.

[2] The second aspect of the present invention is a preferred embodiment for implementing the first aspect of the present invention, characterized by further comprising:

a drive mechanism for moving the moving frame;
a drive mechanism for moving the filter test device in the moving frame;

setting means for setting a scanning pattern of the filter test device for the exit surfaces of the filter group; and scanning control means for operating each of the drive mechanisms so that the filter test device is caused to scan/move in accordance with the scanning pattern that is set by the setting means.

With this configuration, a filter test device is caused to automatically scan/move in a prescribed scanning pattern, and the filters can be tested by merely setting the prescribed scanning pattern of the filter test device in relation to the exit surfaces of the filter group in accordance with content of the test. The filters in a clean room can thereby be more easily tested and the test efficiency can be further increased.

[3] The third aspect of the present invention is a preferred embodiment for implementing the first aspect of the present invention, characterized by further comprising:

a guide concavity disposed on each of the walls across which the moving frame extends, to extend in the moving frame movement direction; and a guide mechanism disposed inside the guide concavity for guiding the moving frame, and a drive mechanism disposed also inside the guide concavity for moving the moving frame.

With this configuration, purified air discharged from the exit surfaces of the filter group can be prevented from being disturbed by the presence of the guide and drive mechanisms, compared with the above-described guide and drive mechanisms exposed in the room. A reduction in room purity due to disturbances in the air flow can thereby be prevented during normal use of the clean room, and room purity can be kept at a high level. Also, a reduction in the test accuracy due to disturbances in the air flow during filter testing can be prevented and high-precision testing can be carried out.

There are cases in which the filter test device cannot move to the ends of the moving frame in the longitudinal direction for structural reasons, and the movement range of the filter test device in the longitudinal direction of the moving frame is somewhat shorter than the length of the moving frame. In such cases, the guidance mechanism is set inside the guide concavity as described above, and the guiding of the ends of the moving frame in the longitudinal direction is carried out inside the guide concavity. The ends of the moving frame in the longitudinal direction, which are separated from the movement range of the filter test device, are thereby disposed inside the guide concavity, the movement range of the filter test device in the longitudinal direction of the moving frame can be assured to include the two ends portions in the longitudinal direction of the moving frame of the exit surfaces of the filter group, and both ends of the exit surfaces can be suitably tested.

[4] The fourth aspect of the present invention is a preferred embodiment for implementing the third aspect of the present invention, characterized by further comprising an openable/closable cover for covering up the guide concavity.

With this configuration, the cover is opened during filter testing, and movement of the moving frame is allowed under the guidance of the guidance mechanism housed in the guide concavity. The cover is closed when the clean room is in normal service, whereby disturbance of the air flow due to the presence of a concavity in the room wall can be prevented, and dust can be prevented from remaining in the concavity. The purity of the room can thereby be kept at a high level when the clean room is in normal service.

[5] The fifth aspect of the present invention is a preferred embodiment for implementing the third aspect of the present invention, characterized by further comprising suction means for sucking and exhausting air from the interior of the guide concavity With this configuration, even if dust is produced by the guidance and drive mechanisms housed in the guide concavity when the moving frame is moved during filter testing, the dust can be prevented from flowing into the room by using the above-described air sucking. A reduction in the testing precision due to dust flowing out from the guide concavity can be prevented, and filter testing can be carried out with higher precision.

[6] The sixth aspect of the present invention is a preferred embodiment for implementing the first aspect of the present invention, characterized in that the filter group is disposed in the ceiling of the clean room;

a curved streamline area is formed in which area the air flow velocity is higher than in other areas inside the room at locations proximal to the two sides in the movement direction of the moving frame as viewed in the longitudinal direction of the moving frame, when the uniform discharge of the supplied air is blown in a parallel downward flow from the exit surfaces of the filter group; and the filter test device is mounted on the moving frame in an extended supported state to be positioned in the fringe part or outside the curved streamline area in the movement direction of the moving frame of the curved streamline area, as viewed in the longitudinal direction of the moving frame.

In other words, the flow of the supplied air uniformly discharged in a parallel downward flow into the room from the exit surfaces of the filter group is analyzed. As a result, eddy flow areas A1, A2 in which the air flow is disturbed because the moving frame 9 is an obstacle to the supplied air SA discharged from the exit surfaces of the filter group are formed on the upper and lower surfaces of the moving frame 9 as viewed in the longitudinal direction of the moving frame, as shown in FIG. 8. For this reason, the conventional apparatus described above is configured so that a filter test device 10 is positioned in the upper and lower vicinities of the moving frame 9 as viewed in the longitudinal direction of the moving frame. In this apparatus, the filter test device 10 is easily affected by disturbances in the air flow in the upper eddy area A1. Therefore, the test results tend to be inaccurate and unstable in tests of the supplied air SA discharged from the exit surfaces of the filter group using conventional equipment.

It is confirmed, as shown in FIG. 8, that curved streamline areas B1, B2, in which streamlines are curved and the air flow velocity is greater than the other areas C in the room because the supplied air SA is discharged in parallel downward streams from the exit surfaces of the filter group, are formed in locations proximal to the two sides of the moving frame 9 in the movement direction (i.e., the forward and rearward areas in the movement direction of the moving frame 9). It is therefore apparent that the test results tend to become inaccurate and unstable due to the effect of the curved streamline area B1 (or B2) if the support position of the filter test device 10 is changed to the side area of the moving frame 9 as viewed in the longitudinal direction of the moving frame so as to avoid the effect of the eddy areas A1, A2.

In contrast, in accordance with the configuration of the sixth aspect (see FIG. 8), the support device that supports the filter test device 10 is made as short a possible to avoid a reduction in the test accuracy due to shaking of the filter test device 10. Based on the results of the analysis described above, it is possible to stably obtain, in tests of the supplied air SA discharged from the exit surfaces of the filter group, substantially the same accurate results as in a case in which the filter test device 10 is disposed in another area C (i.e., area in which the supplied air SA is discharged in a stable parallel downward flow) of the room that is considerably separated from the moving frame 9, because the filter test device 10 is mounted on the moving frame 9 in an extended supported state positioned in the fringe part B1' (or B2') of the curved streamline area B1 (or B2) in the movement direction of the moving frame as viewed in the longitudinal direction of the moving frame, or in the external area C1' (or C2') of the curved streamline area B1 (or B2) in the vicinity of the fringe part.

Another method that may be considered to avoid the effect of the eddy current areas A1, A2 and the curved streamline areas B1, B2 is to increase the distance between the filter test device 10 and moving frame 9 in the height direction, and to support/mount the filter test device 10 on the moving frame 9 in a position that is in the upper fringe part of the upper eddy current area A1 or above and outside the upper eddy current area A1 in the vicinity of the upper fringe part. In this case, however, a considerable distance must be assured in the height direction between the moving frame 9 and the exit surfaces of the filter group. The in-room installation height of the moving frame 9 is reduced by an equivalent amount and the efficiency of the testing work tends to be reduced, because the equipment installed in the room more often becomes an obstacle to the movement of the moving frame 9. Applicability problems also arise in many cases (e.g., the case shown in the later-described FIG. 15) in which it is difficult to increase the distance itself in the height direction between the moving frame 9 and the filter test device 10, because the distance in the height direction between the moving frame 9 and the exit surfaces of the filter group is limited due to architectural conditions and other factors of the clean room.

In contrast, in accordance with the configuration of the sixth aspect, there is no need to secure a large distance in the height direction between the moving frame 9 and the exit surfaces of the filter group in the manner of the alternative method described above, because the filter test device 10 is mounted on the moving frame 9 in an extended supported state in the movement direction of the moving frame. This makes it possible to avoid the problem described above in which equipment installed in the room often becomes an obstacle to the movement of the moving frame 9 and the testing efficiency is reduced, and to avoid the applicability problems described above. At the same time, accurate test results can be stably obtained in the testing of the supplied air SA discharged from the exit surfaces of the filter group.

The configuration of the sixth aspect of the present invention can be implemented in cases in which the discharge surfaces 4a (the filter surfaces on the side directly facing the room interior) of the filter group G on the ceiling are used as the exit surfaces of the filter group G, and a pure supplied air SA is discharged in parallel downward streams from the discharge surfaces 4a of the filter group G into the room, as shown in FIGS. 15 and 16. The same applies to cases in which an air-permeable ceiling partition 6 is disposed below the filter group G, the lower surface 6a of the ceiling partition 6 is used as the exit surface of the filter group G, and supplied air SA is discharged in parallel downward streams from the filter group G into the room through the ceiling partition 6, as shown in FIGS. 2 and 4.

In other words, the arrangements shown in FIGS. 2 and 4 are examples in which the moving frame is disposed below the ceiling partition 6 by using the lower surface 6a of the ceiling partition 6 as the exit surface of the filter group G. On the other hand, the arrangement shown in FIG. 15 is an example in which the moving frame 9 is disposed between the filter group G and the ceiling partition 6 by using the discharge surfaces 4a of the filter group G as the exit surfaces of the filter group G.

[7] The seventh aspect of the present invention is a preferred embodiment for implementing the sixth aspect of the present invention, characterized in that the filter test device is mounted on the moving frame in a supported state positioned to one lateral side of the moving frame at substantially the same height as the moving frame, as viewed in the longitudinal direction of the moving frame; and the distance between the moving frame and the filter test device in the movement direction of the moving frame is 75 mm to 250 mm.

In case of a clean room (a clean room or other room typically used in manufacturing pharmaceuticals and electronic components) in which supplied air from the exit surfaces of the filter group is uniformly blown downward in parallel streams, the discharge velocity of air supplied from the exit surfaces of the filter group is commonly set to about 0.3 to 0.6 m/s. In the analysis described above, however, when the configuration of the seventh aspect described above was adopted under such air discharge velocity conditions, the filter test device was found to have essentially the same extended supported state (i.e., a supported state positioned in the fringe part or outside the curved streamline area in the movement direction of the moving frame of the curved streamline area as viewed in the longitudinal direction of the moving frame) as that described above in the configuration of the sixth aspect under conditions in which the filter test device is at substantially the same height as the moving frame.

Therefore, in accordance with the configuration of the seventh aspect, when the discharge velocity of air supplied from the exit surfaces of the filter group is about 0.3 to 0.6 m/s, additional work for identifying the position of the curved streamline area around the moving frame by obtaining precise air velocity measurements can be eliminated, even though the filter test device is mounted on a moving frame in the extended supported state described above. This feature can make it easier to implement the configuration of the sixth aspect.

In implementing the sixth aspect of the present invention, the distance between the moving frame and the filter test device in the movement direction of the moving frame is defined as the distance in the movement direction of the moving frame between the moving frame and the side surface of the filter test device in the moving frame.

In implementing the configuration of the sixth aspect, the distance between the moving frame and the filter test device in the movement direction of the moving frame is preferably 100 mm to 250 mm, and is more preferably 150 mm to 250 mm.

[8] The eighth aspect of the present invention is a preferred embodiment for implementing the sixth aspect of the present invention, characterized in that the distance in the height direction between the exit surfaces of the filter group disposed in the ceiling of the clean room and the filter test device is 100 mm or more.

In accordance with the analysis described above, there are no strong air disturbances in comparison with the above-described eddy currents and curved streamline areas in locations that are very close to the exit surfaces of the filter group, even under the exit surfaces of the filter group. Although the strength level differs slightly due to differences in the performance and material of the filter parallel disposed in the ceiling of the clean room, it was found that a weak air disturbance is constantly present due to members (the presence of the filters and the above-described ceiling partition themselves) constituting the exit surfaces of the filter group from which supplied air is blown downward in parallel streams.

As described above, in a clean room in which supplied air is uniformly blown downward from the exit surfaces of the filter group into the room in parallel streams, the discharge velocity of air supplied from the exit surfaces of the filter group is commonly set to about 0.3 to 0.6 m/s, but in the case of such air discharge velocity conditions, the above-described weak air disturbances below the exit surfaces of the filter group were observed in a maximum range of about 80 mm below the exit surfaces of the filter group.

In contrast, in accordance with the configuration of the eighth aspect and based on the results of the analysis described above, the filter test device can adequately function while avoiding the effect of weak air disturbances as described above. These disturbances are due to the presence of members (i.e., the filters and ceiling partition) themselves constituting the exit surfaces of the filter group. The improvement is possible because the distance between the exit surfaces of the filter group and the filter test device is 100 mm or more in the height direction. The desired object of the present invention can be even more efficiently achieved in that accurate test results are thereby stably obtained in the testing of supplied air discharged from the exit surfaces of the filter group.

[9] The ninth aspect of the present invention is a preferred embodiment for implementing the sixth aspect of the present invention, characterized in that a frame-accommodating concavity is disposed in the room walls positioned at the ends of the moving frame in the movement direction for accommodating the moving frame via movement to extend from a position corresponding to the exit surfaces of the filter group.

In other words, when the filter test device is mounted on the moving frame in the extended supported state described above, an area that cannot be tested is produced in which the filter test device cannot be positioned directly under the ceiling surface in the vicinity of one of the room walls (i.e., an area into which a filter test device supported in a stretched state cannot be moved) when the moving frame is moved to a position proximate to one of the room walls positioned on the side opposite from the filter test device as viewed in the longitudinal direction of the moving frame. In such a configuration, the technique in which the filter test device is essentially mounted on the moving frame in an extended supported state can still be adopted by providing a frame-accommodating concavity, and non-testable areas can be eliminated and accurate test results stably obtained in the testing of supplied air discharged from the exit surfaces of the filter group while avoiding the effect of the curved streamline area and eddy current area, even in areas (areas close to one of the room walls described above) corresponding to the non-testable areas. This makes it possible to provide a filter test device with an even more excellent function for testing supplied air discharged from the exit surfaces of the filter group.

The moving frame is accommodated in the frame-accommodating concavity when the clean room is in normal service, whereby disturbances in the air discharged from the exit surfaces of the filter group due to the presence of a moving frame can be prevented in comparison with leaving the moving frame disposed between the walls. A reduced level of room purity due to air disturbances can thereby be prevented, and the level of purity in the clean room can be kept high when the room is in normal service.

The moving frame is accommodated in the frame-accommodating concavity described above by extending [the moving frame] from a position corresponding to the exit surfaces of the filter group. Therefore, room cleanup following completion of filter testing, preparations for testing, and other additional work can be considerably reduced in comparison with adopting a mode in which the moving frame is dismounted when the clean room is to be placed in normal service.

[10] The tenth aspect of the present invention is a preferred embodiment for implementing the ninth aspect of the present invention, characterized in that a drive mechanism is disposed inside the frame-accommodating concavity for moving the moving frame.

With this configuration, the supplied air discharged from the exit surfaces of the filter group can be prevented from being disturbed due to the presence of the drive mechanism when the filters are tested and when the clean room is in normal service, in the same manner as the third aspect of the present invention. A reduction in the purity level of the room due to disturbances in the air flow can thereby be more efficiently prevented when the clean room is in normal service. A reduction in the test precision due to disturbances in the air flow can be prevented during filter testing, and high precision testing can be carried out.

[11] The eleventh aspect of the present invention is a preferred embodiment for implementing the ninth aspect of the present invention, characterized by further comprising an openable/closable cover for covering up the frame-accommodating concavity.

With this configuration, air flow disturbances due to the presence a concavity in the wall can be prevented, as can the presence of dust in the concavity, in the same manner as when a cover is used for the guide concavity in the fourth aspect of the present invention. This can be achieved by closing the cover when the clean room is in normal service. The purity of the room can thereby be kept at a higher level when the clean room is in normal service.

[12] The twelfth aspect of the present invention is a preferred embodiment for implementing the ninth aspect of the present invention, characterized in that the filter test device is supported/mounted on the moving frame to be offset to the side opposite from the frame-accommodating concavity from a width center of the moving frame in the movement direction of the moving frame.

With this configuration, there is a limit to the movement range of the moving frame on the side opposite from the frame-accommodating concavity, and there are cases in which the moving frame cannot move to a location where the width center of the moving frame in the movement direction of the moving frame is positioned so as to correspond to the edge area opposite from the frame-accommodating concavity side, which is one of the two edge areas of the exit surfaces of the filter group. Even in such cases, a range that includes the edge area opposite from the frame-accommodating concavity side, which is one of the two edge areas of the exit surfaces of the filter group, can be assured as the movement range of the filter test device produced by the movement of the moving frame, and the edge area can also be suitably tested by mounting the filter test device to one side of the moving frame in the manner described above.

The frame-accommodating concavity is used to allow all or a part of the moving frame to enter into the frame-accommodating concavity by using the extended movement described above. A range that includes the edge area opposite from the frame-accommodating concavity side, which is one of the two edge areas of the exit surfaces of the filter group, can thereby be assured as the movement range of the filter test device produced by the movement of the moving frame, and the edge area can also be suitably tested by adopting a structure in which the filter test device is mounted on the moving frame on the side opposite from the frame-accommodating concavity side in the manner described above.

[13] The thirteenth aspect of the present invention is a preferred embodiment for implementing the sixth aspect of the present invention, characterized in that supported state switching means is provided for switching the supported state of the filter test device in the moving frame between an extended supported state, and a retracted supported state in which the filter test device is positioned nearer to the moving frame than in the extended supported state in the moving direction of the moving frame.

When the filter test device is mounted on the moving frame in an extended supported state, an area that cannot be tested is produced in which the filter test device cannot be positioned directly under the ceiling surface in the vicinity of one of the room walls (i.e., an area into which a filter test device supported in a stretched state cannot be moved) when the moving frame is moved to a position proximate to one of the room walls positioned on the side opposite from the filter test device as viewed in the longitudinal direction of the moving frame. In accordance with the configuration of the thirteenth aspect, on the other hand, the filter test device is brought close to the moving frame by switching from an extended supported state to a retracted supported state by using supported state switching means. Therefore, the filter test device can be brought into close proximity to a position nearby one of the room walls.

In addition to the supported state switching means, a frame-accommodating concavity may be formed for accommodating the moving frame by extending the frame in the movement direction in the room toward the room wall positioned on the side opposite from the filter test device as viewed in the longitudinal direction of the moving frame. As a result, formation of the curved streamline areas and eddy currents can be eliminated and the filter test device when in a retracted supported state can be prevented from being affected by curved streamline areas and eddy currents. This is achieved by accommodating the moving frame in the frame-accommodating concavity when the filter test device is brought into close proximity to the moving frame by switching to a retracted supported state.

In order to eliminate the non-testable areas described above and to avoid the effect of the curved streamline areas and eddy currents when locations corresponding to such non-testable areas are to be tested, it is possible to adopt another method in which the moving frame is accommodated in the frame-accommodating concavity, whereby the filter test device can be brought close to a position extremely proximal to of the walls while the filter test device remains in an extended supported state. In such a case, however, the depth dimension (i.e., the deepness of the concavity) of the frame-accommodating concavity in the movement direction of the moving frame must be made fairly large, and this produces a considerable restriction in terms of constructing a clean room.

In contrast, with a structure in which supported state switching means and a frame-accommodating concavity are provided, the filter test device can be brought close to a position extremely proximal to one of the room walls by accommodating the moving frame in the frame-accommodating concavity and bringing the filter test device close to the moving frame by switching to a retracted supported state. In comparison with the above-described other method, the depth dimension of the frame-accommodating concavity in the movement direction of the moving frame can be reduced, the restriction conditions in terms of clean room construction can be eased, and excellent applicability can be achieved.

[14] The fourteenth aspect of the present invention is a preferred embodiment for implementing the thirteenth aspect of the present invention, characterized in that:

a supporting device, acting as the supported state switching means oriented so as to extend from the moving frame to the side opposite from the room wall provided with a frame-accommodating concavity for accommodating the moving frame by extending the frame from a position corresponding to the exit surfaces of the filter group as viewed in the longitudinal direction of the moving frame, has a structure that can extend and contract between a stretched state in which the filter test device is in an extended supported state, and a contracted state in which the filter test device is in a retracted supported state; and the supporting device has a structure for switching the supporting device from the stretched state to the contracted state by moving the moving frame toward a contacted wall in a state in which, by extending the frame from a position corresponding to the exit surfaces of the filter group, after the distal end of the supporting device is brought into contact with the room wall that is opposite from the room wall provided with a frame-accommodating concavity for accommodating the moving frame.

In accordance with the fourteenth aspect, the moving frame is moved toward the room wall opposite from the room wall in which the frame-accommodating concavity is formed, the distal end of the supporting device makes contact with the opposing wall, and the supporting device is switched from a stretched state to a contracted state, whereby the filter test device can be switched from an extended supported state to a retracted supported state. Therefore, the switch between an extended supported state and a retracted supported state can be easily carried out in comparison with a case in which the supporting device switching means is a structure in which the filter test device is switched from an extended supported state to a retracted supported state by exchanging the supporting device or by manually operating the retractable supporting device to switch to a contracted state.

In implementing the fourteenth aspect of the present invention, the operation for switching the filter test device from a retracted supported state to an extended supported state can be carried out by adopting an operation mode in which the supporting device is switched by manual operation from a contracted state to a stretched state, an operation mode in which the supporting device is switched by a dedicated actuator from a contracted state to a stretched state, or a variety of other operation modes.

In order to switch the filter test device from an extended supported state to a retracted supported state by switching the contractible supporting device between a stretched state and a contracted state, it is possible to consider a method in which a dedicated actuator is used to switch the supporting device to a stretched state and a contracted state. In this case, however, the operating mechanism for the dedicated actuator for switching to either state is made more complicated. In contrast, in accordance with the fourteenth aspect, the operation mechanism for the dedicated actuator can be simplified in comparison with the other method described above even when a dedicated actuator is used for switching the supporting device, because the operation performed by the dedicated actuator is achieved by merely switching the supporting device to a stretched state.

[15] The fifteenth aspect of the present invention is a preferred embodiment for implementing the sixth aspect of the present invention, characterized by further comprising a cable-shaped component holding mechanism for holding a cable-shaped component that extends from the filter test device along the moving frame while allowing the filter test device to move in relation to the moving frame.

With this configuration, cable-shaped components can be efficiently prevented from becoming caught on equipment installed in the room and interfering with work, in comparison with moving the filter test device in a state in which the cable-shaped components extended from the filter test device are left dangling.

In the case of leak testing, a tube for transporting sampled air that has been sucked/captured by the filter test device is required as a cable-shaped component that extends from the filter test device. Excessive bending of the tube can be prevented and impediments to leak testing due to impaired air transport caused by excessive bending can be prevented by holding this tube aligned with the moving frame using the cable-shaped component holding mechanism. The testing of the filters of the clean room can thereby be more smoothly carried out.

[16] The sixteenth aspect of the present invention is a preferred embodiment for implementing the sixth aspect of the present invention, characterized by further comprising a cable-shaped component holding mechanism for holding a cable-shaped component extended between the moving frame and the room wall along the room wall while allowing the moving frame to move.

In accordance with this configuration, in the same manner as the fifteenth aspect of the present invention, cable-shaped components can be efficiently prevented from becoming caught on equipment installed in the room and interfering with work, in comparison with moving the moving frame in a state in which the cable-shaped components extended between the moving frame and the room wall are left dangling. In the case of leak testing, situations can be prevented in which the tube as a cable-shaped component is excessively bent and the leak test is adversely affected by impaired air transport, or the like. The testing of the filters of the clean room can thereby be more smoothly carried out.

[17] The seventeenth aspect of the present invention is a preferred embodiment for implementing the sixth aspect of the present invention, characterized by further comprising:

a guidance structure having a guide rail provided to the room walls spanned by the moving frame to extend in the movement direction of the moving frame, and bear the two ends of the moving frame in the longitudinal direction in the moving device for moving along the guide rail under the guidance of the guide rail; and an adapting mechanism provided on at least one of the two ends of the moving frame in the longitudinal direction for allowing the moving frame and the moving device to move relative to each other in the longitudinal direction of the moving frame, or allowing the moving frame and the moving device to rotate relative to each other.

With this configuration, slippage due to movement and rotation of the moving frame and the moving device in relation to each other can be absorbed by the adapting mechanism even if some slippage is generated between the moving frame and the guide rails due to aging, earthquakes, and other factors, and smooth movement of the moving frame under the guidance of the guide rails can be maintained. In view of these points, a filter test device that has excellent durability and simple maintenance can be obtained.

[18] The eighteenth aspect of the present invention is a preferred embodiment for implementing the sixth aspect of the present invention, characterized by further comprising:

a detachable air-permeable ceiling partition disposed below a filter group provided to the ceiling of the clean room, for supplying air discharged from the filter group downward into a clean room in parallel streams through the ceiling partition;

wherein the lower surface of the ceiling partition is used as the exit surface of the filter group so that the moving frame is disposed below the ceiling partition.

In other words, in accordance with the eighteenth aspect, the moving frame and filter test device are movably operated below the ceiling partition to test (e.g., for air velocity) the supplied air discharged from the ceiling partition, and the supplied air discharged from the filters can be tested (e.g., for leaks) by movably operating the moving frame and the filter test device in a state in which the detachable ceiling partition has been removed. This arrangement allows the testing function to be further improved.

[19] The nineteenth aspect of the present invention is a preferred embodiment for implementing the sixth aspect of the present invention, characterized by further comprising:

a supplied air chamber that supplies air to the clean room through the filter group and is disposed on the reverse side of the filter group;

mixing means for mixing filter leak testing powder with the air that passes through a duct for supplying air to the supplied air chamber; and downstream measurement means for sucking/capturing air from all test locations on the exit surfaces of the filter group by using a downstream suction device, and measuring the amount of powder particles in the captured air;

wherein the mixing means includes:

production means for receiving a supply of production gas from first air supply means and producing the powder in a state dispersed in the production gas;

diluting means in which the powder outputted together with the production gas from the production means is joined to and diluted with a diluting gas supplied from second air supply means; and dispersion means for dispersing the powder outputted together with the production gas, and the diluting gas from the diluting means in the air passing through the supplied air duct.

With this configuration, diffusion of the powder to be mixed in the air that passes through the supplied air duct after dispersion can be facilitated by diluting the powder with the diluting gas of in the diluting means. The dilution is performed more efficiently than in a conventional apparatus in which the generating powder in the production means is merely allowed to flow unchanged into the supplied air duct. Facilitating the diffusion in this manner prevents variability in the powder concentration in the supplied air chamber, and the powder concentration inside the supplied air chamber can be made uniform with high efficiency.

Test errors due to variability of the powder concentration in the supplied air chamber can thereby be prevented when the filters are tested for leaks. In these tests, air is sucked/captured from the downstream suction device from all test locations of the exit surfaces of the filter group in the clean room, and the amount of powder particles (amount of powder leaked) in the captured air is measured using downstream measurement means. The test accuracy of the filter leak test can thereby be increased more efficiently in comparison with a conventional apparatus.

In order to minimize testing errors caused by variability of the powder concentration in the supplied air chamber in a conventional apparatus, the powder is allowed to diffuse under natural conditions in the supplied air chamber, and the system must wait until the powder concentration in the supplied air chamber becomes uniform, which requires a considerably wait time. In accordance with the nineteenth aspect, however, the powder concentration in the supplied air chamber can be efficiently made uniform as described above, and such a waiting time can be reduced. The testing efficiency of filter leak testing can thereby be increased.

[20] The twentieth aspect of the present invention is a preferred embodiment for implementing the nineteenth aspect of the present invention, characterized in that:

the diluting means includes an agitation container for receiving an inflow of the diluting gas supplied from the second air supply means and the production gas outputted together with the powder from the production means;

a revolving air stream is produced inside the agitation container by spraying one or both of the diluting gas and production gas in the interior of the agitation container in a state in which the gases are caused to follow the internal peripheral surface of the agitation container during the inflow of the diluting gas and the production gas into the container; and the powder that flows into the agitation container together with the production gas is mixed and diluted with the diluting gas by using the revolving air stream.

With this configuration, the powder can be more uniformly and efficiently diluted in comparison with merely merging a diluting gas with a production gas outputted together with the powder from the production means by using a merging pipe or the like as a diluting mode. Therefore, the diffusion of the mixed powder in the air that passes through the supplied air duct is more efficiently facilitated, the powder concentration in the supplied air chamber is made more uniform by the improved diffusion, and improvement in the test accuracy of filter leak testing can be more efficiently attained.

[21] The twenty-first aspect of the present invention is a preferred embodiment for implementing the nineteenth aspect of the present invention, characterized by further comprising: dual-use air supply means that doubles as first air supply means and second air supply means;

wherein gas outputted from the dual-use air supply means is branched into streams, and one branched gas is supplied to the production means as the production gas; and the other branched gas is supplied to the diluting means as the diluting gas.

With this configuration, the apparatus structure can be simplified, equipment costs can be reduced, and apparatus maintenance can be simplified in comparison with separately providing first air supply means for feeding production gas and second air supply means for feeding diluting gas as dedicated devices.

[22] The twenty-second aspect of the present invention is a preferred embodiment for implementing the nineteenth aspect of the present invention, characterized by further comprising:

a production flow rate controller for controlling the feed flow rate of production gas to the production means; and a diluting flow rate controller for controlling the feed flow rate of diluting gas to the diluting means.

With this configuration, the amount of powder produced in the production means and the powder concentration in the supplied air chamber can be controlled in accordance with the testing conditions or other factors by controlling the feed flow rate of the production gas in the production means by using a production flow rate control valve.

Also, the flow rate at which the diluting gas is fed to the diluting means can be controlled by using a diluting flow rate control valve to control the extent to which the powder is diluted in the diluting means. The desired effect can be reliably obtained in terms of facilitating the diffusion of the mixed powder in the air that passes through the supplied air duct, while eliminating unnecessary supply of diluting gas in response to changes in the amount of powder produced.

[23] The twenty-third aspect of the present invention is a preferred embodiment for implementing the nineteenth aspect of the present invention, characterized in that:

the dispersion means includes a plurality of spray nozzles disposed in the supplied air duct so as to be distributed in the longitudinal direction of the duct cross-sectional shape thereof, and the powder outputted together with the production gas and the diluting gas from the diluting means is distributed to the plurality of spray nozzles and sprayed from the spray nozzles.

With this configuration, diffusion of the mixed powder in the air that passes through the supplied air duct can be more efficiently facilitated using an effect that combines the dilution of the powder by the diluting means. An improvement is achieved in comparison with merely allowing the powder to flow in from a single location in the supplied air duct, as in a conventional apparatus. Improvement in the test accuracy can thereby be more efficiently achieved by ensuring a uniform concentration of the powder inside the supplied air chamber.

Also, powder diffusion can be particularly efficiently facilitated in the longitudinal direction of the duct cross-sectional shape because a plurality of spray nozzles is disposed so as to be distributed in the longitudinal direction of the duct cross-sectional shape in the supplied air duct. This is particularly effective when the supplied air duct is given a flat, wide cross-sectional shape having about the same width dimension as the supplied air chamber for the purpose of uniformly feeding air to the clean room.

[24] The twenty-fourth aspect of the present invention is a preferred embodiment for implementing the nineteenth aspect of the present invention, characterized by further comprising a collision member disposed further downstream in the duct from the powder-dispersing location of the dispersion means, for causing powder dispersed from the dispersion means to collide and disperse in the supplied air duct.

With this configuration, it is possible to more efficiently facilitate the diffusion of the mixed powder in the air that passes through the supplied air duct and to make the powder concentration in the supplied air chamber uniform by diffusing the dispersed powder by using the collision against the collision member.

[25] The twenty-fifth aspect of the present invention is a preferred embodiment for implementing the sixth aspect of the present invention, characterized by further comprising:

a supplied air chamber disposed on the reverse side of the filters for feeding air to the clean room through the filters;

mixing means for mixing filter leak testing powder with the air that passes through a duct for supplying air to the supplied air chamber;

downstream measurement means for sucking/capturing air from all test locations on the exit surfaces of the filter group by using a downstream suction device and measuring the amount of powder particles in the captured air;

a plurality of upstream suction devices disposed in a distributed manner over the entire area of the chamber interior areas in the direction of alignment of the filters in the filter group, for sucking/capturing air of all chamber interior areas in the supplied air chamber;

suction device switching means for selecting whether to suction/capture air from any of the plurality of upstream suction device; and upstream measurement means for sucking/capturing air by using the upstream suction device selected by the suction device switching means, and measuring the amount of powder particles in the captured air as information for compensating the amount of particles measured by the downstream measurement means or as information for controlling the amount in which the powder is mixed by the mixing means.

With this configuration, the same test accuracy can be obtained as when filters are tested for leaks in a state in which the powder concentration inside the air supply chamber is uniform. This can be achieved even when variability occurs in the powder concentration inside the air supply chamber, and the method used involves compensating the amount of particles measured by the downstream measurement means based on the amount of particles measured by the upstream measurement means, or controlling the amount of powder mixed by the mixing means based on the amount of particles measured by the upstream measurement means. The test accuracy of a filter leak test can thereby be efficiently increased in comparison with a conventional apparatus.

In the case of the above-described correction, air from all test locations of the exit surfaces of the filter group is sucked/captured by a downstream suction device, and the amount of powder particles in the captured air is measured by the downstream measurement means. In correlation with the above, upstream test devices selected from a plurality of upstream test devices and positioned in the corresponding air suction locations of the downstream suction devices are sequentially selected by the suction device switching means. The amount of powder particles in the air sucked/captured by the selected upstream suction devices is measured by the upstream measurement means. The amount of particles measured by the downstream measurement means in all test locations is corrected and converted, based on the amount of particles measured by the upstream measurement means, to the amount of particles present when the powder concentration inside the air supply chamber is at a prescribed concentration. The same test accuracy can thereby be obtained as when filters are tested for leaks in a state in which the powder concentration inside the air supply chamber is uniform, and [this result can be achieved] despite actual variability in the powder concentration inside the air supply chamber.

To correct the mixing amount in this manner, air from all test locations of the exit surfaces of the filter group is sucked/captured by a downstream suction device, and the amount of powder particles in the captured air is measured by the downstream measurement means. In correlation with the above, upstream test devices are selected from the plurality of upstream test devices and positioned in corresponding air suction locations of the downstream suction devices are sequentially selected by the suction device switching means. The amount of powder particles in the air sucked/captured by the selected upstream suction devices is measured by the upstream measurement means. The amount of powder to be mixed by the mixing means can be controlled so that the amount of particles measured by the upstream measurement means in all test locations is brought to a required set value (i.e., a required set powder concentration) based on the measurement results of the upstream measurement means. The same test accuracy can thereby be obtained as when filters are tested for leaks in a state in which the powder concentration inside the air supply chamber is uniform, and [this result can be achieved despite actual variability in the powder concentration inside the air supply chamber.

BEST MODE FOR CARRYING OUT THE INVENTION

FIGS. 1, 2, and 4 show a clean booth for testing an air purification filter for an interior room. A grid-like filter support frame 3, as shown in FIG. 3, is disposed in a ceiling of a clean room 2 formed in a booth 1, and numerous high-performance filters 4 (e.g., HEPA filters and ULPA filters) are aligned in a matrix arrangement in the horizontal direction in the entire ceiling by being supported by the filter support frame 3. The space on the other side of the ceiling above a filter group G acts as a supplied air chamber 5 for supplying air to the clean room 2 through the filter group G. Supplied air SA is supplied to the supplied air chamber 5, whereby the supplied air SA is purified by the filters 4 and uniformly blown downward in a parallel flow from a discharge surface 4a of the filters 4.

A horizontally oriented air-permeable ceiling partition 6 composed of a perforated panel is disposed below the filter group G across the entire ceiling of the clean room 2. The lower surface 6a of the ceiling partition 6 acts as the exit surface of the filter group G during normal use of the clean room 2, and the purified supplied air SA discharged from the filters 4 is blown uniformly downward in a parallel stream into the entire clean room 2 through the ceiling partition 6.

In the booth 1, a circulation channel 8 for connecting the supplied air chamber 5 and an exhaust port 7 disposed in a lower portion of the room wall 2A is formed next to the clean room 2 via the room wall 2A acting as a partition. Circulation fans F1 for circulating the air through the supplied air chamber 5, the clean room 2 and the circulation channel 8 are housed in the circulation channel 8 in the stated sequence.

In other words, clean air that has been purified by the filters 4 in this air circulation is blown downward in a parallel stream from the entire exit surface of the filter group G (i.e., the entire lower surface 6a of the ceiling partition 6), whereby the interior of the clean room 2 becomes a high level clean space suitable for manufacturing medicines and semiconductor components, for example.

The exhaust port 7 is disposed with a series of slits or a plurality of row-like apertures across substantially entire length of the clean room 2 in the longitudinal direction (in a depth direction of each sheet in FIGS. 1, 2 and 4) of the room. The circulation channel 8 is also disposed across a width of the air passage extending across entire length of the clean room 2 in the longitudinal direction. And, a plurality of circulation fans F1 are housed in the circulation channel 8 along the longitudinal direction of the clean room 2. The state of the air flow inside the clean room 2 can thereby be made uniform in the longitudinal direction of the clean room 2, to promote a higher level of purity in the room.

The filters 4 are tested at appropriate times in order to assure the desired purity level in the room. The structure for conducting such a filter test in the booth 1 houses a moving frame 9, which extends across a short side (a right/left direction of the sheet in FIGS. 1, 2, and 4) of the clean room 2 and oriented along the lower surface 6a of the ceiling partition 6. The moving frame 9 is movable along the lower surface 6a of the ceiling partition 6 in a direction orthogonal to the longitudinal direction of the moving frame (i.e., in the longitudinal direction of the clean room 2). The moving frame 9 extends between the opposing walls 2A and 2B of the room in a high position near the lower surface 6a of the ceiling partition 6. And, a filter test device 10 is mounted on the moving frame 9 to be movable in the longitudinal direction of the moving frame 9.

In other words, the filter test device 10 can be moved to any location of the exit surfaces of the filter group G by combining the movement of the moving frame 9 and the movement of the filter test device 10 relative to the moving frame 9, and all of the filters 4 can be efficiently tested via the movement of this test device 10.

Filter testing primarily includes leak testing in which a suction device 10A (downstream suction device) acting as the filter test device 10 is mounted on the moving frame 9, and the supplied air chamber 5 is filled with leak-testing powder (e.g., dioctyl phthalate (DOP) in the form of an aerosol) while the circulation fans F1 are operating. In this state, the amount of particles (i.e., the amount of testing powder that has leaked) in the testing powder contained in the sampled air sucked/captured by the suction device 10A is measured. Filter testing further includes velocity testing of discharged air in which an air velocity sensor 10B, as shown in FIG. 9, acting as the filter test device 10 is mounted on the moving frame 9, and the velocity of air discharged from the filters 4 when the circulation fans F1 are operating is measured. In case of leak testing, the ceiling partition 6 is removed, the discharge surfaces 4a of the filters 4 are used as the exit surfaces of the filter group G, and the suction device 10A, acting as the filter test device 10, is supported at a vertical position near the discharge surfaces 4a of the filters 4. In case of discharge velocity testing, the ceiling partition 6 remains mounted, the lower surface 6a of the ceiling partition 6 act as the exit surfaces of the filter group G, and the air velocity sensor 10B, acting as the filter test device 10, is supported at a vertical distance by 100 mm or more (150 mm in the present embodiment) from the lower surface 6a of the ceiling partition 6.

Leak testing may include testing for leaks in the sealing portion between adjacent filter frames 4A of neighboring filters 4 (i.e., the sealing portions where contact is made between the filter support frame 3 and the two filter frames 4A), testing for leaks in the sealing portion around the filter perimeter between the filter member 4B in each filter 4 and the filter frame 4A that surrounds the filter 4, and testing for leaks in all areas of the filter member 4B of each filter 4.

The reference numeral 11 denotes a powder mixing apparatus for mixing a testing powder P with air that passes through the circulation channel 8 during leak testing; 12 denotes a plurality of upstream suction devices for sucking/capturing air in all areas inside the supplied air chamber 5 during leak testing; and 13 denotes an interior control panel with a controller instrument that automatically moves the filter test device 10. The control panel 13 has a switching valve apparatus 14 that performs a switch to suck/capture the air in the supplied air chamber 5 from any one of the upstream suction devices 12 during leak testing (i.e., sucking/capturing air from any one of locations in the supplied air chamber 5).

The reference numeral 15 denotes a portable computer that is brought into the room during filter testing and is connected to the interior control panel 13 through a connector unit 17 using a connection cord 16. The portable computer 15 controls the movement of the moving frame 9 and the movement of the filter test device 10 relative to the moving frame 9 through the interior control panel 13 during filter testing, whereby the filter test device 10 is caused to automatically scan/move below the exit surfaces of the filter group G in a set scanning pattern that corresponds to the desired test type.

When discharge air velocity testing is performed, its results are automatically processed by the portable computer 15, including sorting, displaying, storing thereof, based on the air velocity detection information sequentially inputted from an air velocity sensor 10B through the cord 18 to the computer 15 through the interior control panel 13.

In the case of leak testing, on the other hand, the suction device 10A (downstream suction device) acting as the filter test device 10 is caused to scan/move, and the portable computer 15 automatically controls the switching of the switching valve apparatus 14 in the interior control panel 13 in accordance with the movement of the suction device 10A so that air inside the supplied air chamber 5 is selectively sucked/captured from the upstream suction devices 12 in positions that correspond to the movement position of the suction device 10A.

In leak testing, together with the scanning and moving of the suction device 10A, downstream sampled air that has been sucked/captured by the suction device 10A is sequentially taken into a downstream dust measuring instrument 20 through a tube 19a and the interior control panel 13, and the amount of particles of the test powder in the downstream sampled air is measured by the downstream dust measuring instrument 20. The upstream sampled air that has been selectively sucked/captured by one of the upstream suction devices 12 correspondingly positioned to the suction device 10A (downstream suction device) is sequentially taken into an upstream dust measuring instrument 21 through the tube 19b and the interior control panel 13, and the amount of particles of the test powder in the upstream sampled air is measured by the upstream dust measuring instrument 21. The test results of the leak test are automatically processed by the portable computer 15, including sorting, displaying and storing thereof, based on the measurement results.

The amount of powder particles in the upstream sampled air measured by the upstream dust measuring instrument 21 is used as test condition correction data so that the test conditions in all test locations make uniform against test errors produced by differences in the amount of powder in the downstream sampled air sucked/captured from all test locations, due to various powder concentrations among various areas of the supplied air chamber 5. Whereby, the amount of powder particles in the downstream sampled air sucked/captured from all test locations can be accurately compared and determined. In more particular, when the test result processing is carried out by the portable computer 15, the amount of particles measured by the downstream dust measuring instrument 20 at each test location is automatically converted and corrected to the amount of particles present if the powder concentration inside the supplied air chamber 5 were at a predetermined concentration.

The powder mixing apparatus 11, as shown in FIGS. 1 and 12, receives a supply of production air CA from a compressor 11A. The apparatus 11 comprises a generator 11B for generating a powder P dispersed in production air CA (e.g., generation of an aerosol from dioctyl phthalate (DOP) stored in a liquid state); a diluter 11C for diluting the powder P outputted together with the production air CA from the generator 11B, by joining, to the powder P, diluting air DA supplied from the compressor 11A via another route; and a dispersing tube 11D for dispersing the powder P outputted from the diluter 11C together with the production air CA and diluting air DA into the air passing through the circulation channel 8, which is a duct for supplying air to the supplied air chamber 5.

In the present embodiment, air outputted from the compressor 11A is branched into streams, one supplied to the generator 11B as production air CA, and the other supplied to the diluter 11C as diluting air DA.

In leak testing, powder P produced in the generator 11B is diluted using the diluting air DA and is then dispersed by the powder mixing apparatus 11 into the air that passes through the circulation channel 8, whereby dispersion of the powder P in the passing air is promoted and the powder concentration inside the supplied air chamber 5 is made uniform. The uniforming process prevents leak testing errors caused by variations in the powder concentrations inside the supplied air chamber.

Since some variations in the concentration is still present inside the supplied air chamber even when the concentration in the chamber has been made uniform by promoting the dispersion, quite high leak testing precision can be obtained overall by the above-described conversion and correction based on the amount of particles measured by the upstream dust measuring instrument 21.

The diluter 11C is composed of an agitation container that agitates and dilutes, with the diluting air DA, the powder P outputted together the production air CA from the generator 11B. Specifically, the production air CA outputted together with the powder P from the generator 11B, and the diluting air DA supplied from the compressor 11A via another route are both sprayed into the cylindrical container along its arcuate internal peripheral surface. A revolving air stream RA is thereby produced inside the container, to efficiently agitate and mix the powder P flown into the container with the production air CA, and uniformly dilute it with the diluting air DA.

The dispersing tube 11D has a structure in which a plurality of spray nozzles X are formed at equidistant intervals in the longitudinal direction of the tube 11D. The tube 11D is oriented to extend in the longitudinal direction of the cross-sectional shape of the circulation channel 8 (i.e., the longitudinal direction of the clean room 2). A plate-shaped collision member 11E for causing a collision with the powder P sprayed from the spray nozzles X of the dispersing tube 11D and dispersing the powder P into the circulation channel 8 is disposed on the downstream side of the powder dispersion position of the dispersing tube 11D in the circulation channel 8. The dispersion of the powder P in the air passing through the circulation channel 8 is more efficiently promoted by spraying and dispersing powder P from the spray nozzles X and dispersing the powder P with collisions on the collision member 11E.

Reference numeral V1 denotes a production flow rate control valve for controlling the flow rate of the production air CA supplied to the generator 11B, and V2 is a dilution flow rate control valve for controlling the flow rate of the diluting air DA supplied to the diluter 11C. The amount of powder produced in the generator 11B (i.e., the amount of powder to be mixed into the air passing through the circulation channel 8) is adjusted by controlling the flow rate of the production air CA supplied from the flow rate control valve V1, and the powder concentration in the supplied air chamber 5 is adjusted. The level of powder dilution in the diluter 11C is adjusted by controlling the flow rate of the diluting air DA supplied from the flow rate control valve V2. The reference numeral V3 is an exhaust control valve for providing overall control by balancing the feed flow rate of the production air CA and the feed flow rate of the diluting air DA.

In sum, in leak testing, the powder mixing apparatus 11 comprises mixing means for mixing the powder P used to test for filter leaks, with air passing through the circulation channel 8 acting as a duct for supplying air to the supplied air chamber 5. The downstream dust measuring instrument 20 comprises downstream measurement means that sucks/captures air from any one of test areas in the exit surfaces of the filter group G using the downstream suction device 10A, and measures the amount of particles of the powder P in the captured air.

In the configuration of the powder mixing apparatus 11, the generator 11B comprises production means for receiving supply of the production air CA from the compressor 11A, and generating the powder P dispersed in the production air CA. The diluter 11C comprises diluting means in which the powder P outputted together with the production air CA from the production means 11B is combined with and diluted by the diluting air DA supplied from the compressor 11A acting as second air supply means. The dispersing tube 11D comprises dispersing means in which the powder P outputted together with the production air CA and diluting air DA from the diluter 11C is dispersed in the air passing through the circulation channel 8, which is a duct for supplying air to the supplied air chamber 5.

The compressor 11A comprises dual-use air supply means that doubles acting as first air supply means for feeding production air CA to the production means 11B and as second air supply means for feeding diluting gas DA to the diluting means 11C.

In leak testing, the switching valve apparatus 14 comprises suction device switching means 14 for selecting, to suck/capture air, any one of the upstream suction devices 12 disposed in a distributed manner over the entire area inside the supplied air chamber 5. The upstream dust measuring instrument 21 comprises upstream measurement means for sucking/capturing air with the one of the upstream suction devices 12 selected by the suction device switching means 14, and measuring the amount of particles of the powder P in the captured air as information for correcting the amount of particles measured by the downstream measurement means 20.

Scanning patterns of the suction device 10A (downstream suction device) in leak testing will be described next. When the inter-frame seals (including the external peripheral seals of the filter group G) are tested for leaks, suction device 10A (downstream suction device) can be continuously moved to any location of the exit surfaces of the filter group G. To take this advantage, in one scanning pattern as shown in FIG. 3(a), the suction device 10A is moved along a straight line at a set speed from one end of the exit surfaces of the filter group G to the other end so as to continuously test for leaks in the inter-frame seals that continue in a straight line across the plurality of filters 4 from one end across to the other end.

When the filter peripheral seal is tested for leaks, another scanning pattern is adopted, as shown in FIG. 3(b), for moving the suction device 10A acting as a filter test device 10 in an annular fashion at a set speed along the filter peripheral seal so as to continuously test for leaks along the entire periphery of the filter peripheral seal between the filter member 4B and its surrounding filter frame 4A for each filter 4. When each area of the filter members 4B is tested for leaks, still another pattern, as shown in FIG. 3(c), is adopted for moving the suction device 10A acting as a filter test device 10 in a serpentine fashion at a set speed all over the exit surfaces of the filter members 4B so as to test for leaks all over the exit surfaces of the filter members 4B for all the filters 4. Both of these scanning patterns are stored in the portable computer 15 by subjecting the portable computer 15 to an initializing operation.

In other words, the portable computer 15 comprises setting means for setting the scanning patterns of the filter test device 10 over the exit surfaces of the filter group G. The portable computer 15 and the control equipment disposed in the interior control panel 13 for automatically moving the test devices comprise scanning control means for operating the drive mechanisms of the test devices and the drive mechanisms for operating the moving frame and test device (to be described in more detail later) so as to scan/move the filter test device 10 in accordance with the set scanning pattern.

The guidance mechanism that guides the movement of the moving frame 9 will be described next. As shown in FIGS. 13 and 14, guide rails 22 extending in the movement direction of the moving frame 9 are disposed in the room walls 2A and 2B spanned by the moving frame 9. Moving devices 23 are provided that move along the guide rails 22 under the guidance of the guide rails 22, respectively. These moving devices 23 accommodate the lengthwise ends of the moving frame 9.

The drive mechanism of the moving frame 9 for moving the moving frame 9 under the guidance of the guide rails 22 is as follows. Timing belts 24 disposed to the sides of the guide rails 22 extend in the movement direction of the moving frame 9, and are connected to the moving devices 23 at a midway point of the belts. An interlocking shaft 26 causes the drive pulleys 25 of the timing belts 24 to rotate in a synchronous manner. A moving frame movement motor 27 for causes the drive pulleys 25 to rotate by the power transmitted from the vicinity of one of the room walls 2A.

To allow the filter test device 10 to move with respect to the moving frame 9, a testing device mover 28 moves along the moving frame 9, with the moving frame 9 itself acting as a guide rail. The filter test device 10 is mounted on the testing device mover 28 through a supporting device 29. The drive mechanism for the testing device for moving the filter test device 10 with respect to the moving frame 9 comprises a timing belt 31 and a motor 33 mounted on the moving frame 9, wherein the timing belt 31 extends in the longitudinal direction of the moving frame 9 and connects to the testing device mover 28 at a midway point thereof. The testing device movement motor 33 is positioned at one end of the moving frame 9 in the longitudinal direction, and the motor 33 causes the drive pulley 32 of the timing belt 31 to rotate.

In other words, the portable computer 15 causes the filter test device 10 to scan/move in the above-described preset scanning patterns over the exit surfaces of the filter group G by using the interior control panel 13 to operate the moving frame movement motor 27 and the testing device movement motor 33.

To bear the ends of the moving frame 9 in the longitudinal direction on the moving device 23, as shown in FIG. 13, a receiving member 34 at the end of the moving frame 9 is mounted on the moving device 23 so as to allow rotation about the vertical Y axis through a bearing 35 to form an adapting mechanism that allows the moving frame 9 and the moving device 23 to move relative to each other in the longitudinal direction of the moving frame, and that allows the moving frame 9 and the moving device 23 to rotate relative to each other about the vertical axis Y, on at least one end of the two ends of the moving frame 9 in the longitudinal direction. The receiving member 34 is provided with rollers 36 that guide displacement of the end portion of the moving frame born on the receiving member 34. Therefore, even if some slippage is generated between the moving frame 9 and guide rails 22 due to aging, earthquakes, and other factors, this can be absorbed by relative movement between the moving frame 9 and moving device 23 produced by the rollers 36, and by relative rotation between the moving frame 9 and moving device 23 produced by rotation about the vertical Y axis of the receiving member 34. Thus, smooth movement of the moving frame 9 under the guidance of the guide rails 22 can be maintained.

The moving frame 9 includes a cableveyor 37A acting as a cable-shaped component holding mechanism for the moving frame 9. The cableveyor 37A holds cable-shaped components that extend from the filter test device 10 (i.e., a tube 19a for transporting sampled air that has been sucked/captured by the suction device 10A during leak testing, an extension cord 18 from the air velocity sensor 10B used in discharge air velocity testing, etc.). The cableveyor 37A retains a position of the filter test device 10 along the moving frame 9 while allowing the filter test device 10 to move in relation to the moving frame 9. One of the room walls 2A spanned by the moving frame 9 is provided with a cableveyor 37B acting as a cable-shaped component holding mechanism for the room wall. The cableveyor 37B holds cable-shaped components between the room wall 2A and the moving frame 9 (i.e., the above-described tube 19a, cord 18, as well as connection cables, etc. connected to the testing device movement motor 33). The cableveyor 37B is placed along the room wall 2A so as to allow the moving frame 9 to move.

The room walls 2A and 2B covered by the moving frame 9 are provided with guide concavities 38 that extend in the movement direction of the moving frame 9. The room wall 2C positioned at one end of the moving frame 9 in its movement direction is provided with a frame-accommodating concavity 39 that accommodates the moving frame 9 by extending the frame 9 from a position corresponding to the exit surfaces of the filter group G. Guide rails 22 as the guide mechanism, timing belts 24 as the moving frame drive mechanism, and a cableveyor 37 for the room walls are disposed inside the guide concavities 38, while the drive pulleys 25, interlocking shaft 26, and moving frame movement motor 27 as a moving frame drive mechanism are disposed inside the frame-accommodating concavity 39.

The guide concavities 38 and the frame-accommodating concavity 39 are provided with openable/closable covers 40 and 41 for covering the concavities 38 and 39, respectively, as shown in FIGS. 4 and 5. Irregularities in the room can be eliminated, disturbances to the air flow in the room can be prevented, and the level of purity in the room can thereby be kept high when the clean room 2 is in normal service by covering the guide concavities 38 and the frame-accommodating concavity 39 using the covers 40 and 41, respectively, when the moving frame 9 is accommodated in the frame-accommodating concavity 39 by the extension movement of the moving frame.

Ventilation holes 42 are formed in the cover 40 of the guide concavities 38 at the ends opposite from the frame-accommodating concavity 39. A concavity exhaust fan F2 is connected to the frame-accommodating concavity 39 through a suction channel 43, and air is suctioned and exhausted from the interior of the guide concavities 38 and the frame-accommodating concavity 39 through the suction channel 43. Even if dust is generated by the equipment housed in the guide concavities 38 and the frame-accommodating concavity 39 (i.e., guide rails 22, moving frame timing belt 24, room wall cableveyor 37, drive pulleys 25, interlocking shaft 26, moving frame movement motor 27, and other components) when the moving frame 9 moves during filter testing, contamination of the room by the generated dust is prevented by the above suction of air, and a reduction in the accuracy of leak testing of the filters caused by such generated dust can be prevented. When the booth 1 is fumigated and the fumigation treatment has been completed, the fumigation gas is discharged outside via an exhaust port 7, and the concavity exhaust fan F2 is operated at the same time to prevent fumigation gas from remaining inside the frame-accommodating concavity 39 and the guide concavities 38 covered by the covers 40 and 41.

The suction device 10A or air velocity sensor 10B, which serves as the filter test device 10, is mounted on the testing device mover 28 through the supporting device 29. Two types of supporting devices 29 are provided, i.e., a dedicated supporting device 29A for the suction device 10A, as shown in FIG. 7, and a dedicated supported device 29B for the air velocity sensor 10B, as shown in FIG. 9. The dedicated supporting devices 29A and 29B can be exchanged to cope with differences in the required distance away from the moving frame and the required distance away from the exit surfaces of the filter group G when performing tests using the suction device 10A and air velocity sensor 10B.

The dedicated suction device supporting device 29A mounts the suction device 10A (downstream suction device)

acting as the filter test device 10 on the moving frame 9 close to the discharge surfaces 4a of the filters 4 acting as the exit surfaces of the filter group G during leak testing, so that the device 10 is somewhat projected from the moving frame 9 toward the side opposite from the frame-accommodating concavity 39 in the width center of the moving frame 9 in the movement direction of the moving frame 9. If a limitation (e.g., a limitation produced by contact between the moving frame 9 and room wall 2D) is thereby imposed on the movement range of the moving frame 9 to the side opposite from the frame-accommodating concavity 39, the moving frame 9 cannot move to a location in which the width center of the moving frame 9 in the movement direction of the moving frame is in position that corresponds to one end edge of the two edges of all the discharge surfaces 4a of the filters 4 on the side opposite from the frame-accommodating concavity 39, as shown in FIG. 3(b) (i.e., the intersecting portion between the room wall 2D and the ceiling surface in the present embodiment). Even in such a case, the movement range of the suction device 10A (downstream suction device) produced by the movement of the moving frame 9 can cover the edge on the side of the room wall 2D.

On the other hand, the dedicated air velocity sensor supporting device 29B mounts the air velocity sensor 10B on the moving frame 9 in an extended supported state so as to be positioned in a fringe part B1' of the curved streamline area B1 in the movement direction of the moving frame of the curved streamline area B1 positioned on the side opposite from the frame-accommodating concavity 39 or positioned in an external location C1' of the curved streamline area B1 in the vicinity of the fringe part. This area B1 is one of the curved streamline areas B1, B2 (see FIG. 8) formed in locations proximal to the two sides in the direction in which the moving frame 9, as viewed in the longitudinal direction of the moving frame, moves in conjunction with the discharge of the supplied air SA from the lower surface of the ceiling partition 6 acting as the exit surface of the filter group G in air velocity testing. Thus, the air velocity sensor 10B is not affected by the curved streamline area B1 or the eddy current areas A1, A2 formed above and below the moving frame 9, and accurate test results can be stably obtained in air velocity testing of supplied air SA discharged from the lower surface of the ceiling partition 6.

The dedicated air velocity sensor supporting device 29B for supporting the air velocity sensor 10B in an extended state on the moving frame 9 has its distal end as a mounting area for the air velocity sensor 10B extending from the moving frame 9 to the side opposite from the frame-accommodating concavity 39 as viewed in the longitudinal direction of the moving frame, as shown in FIG. 9, and can be stretched/retracted in the movement direction of the moving frame 9 by the relative sliding of a plurality of members 30a to 30c that constitute the dedicated air velocity sensor supporting device 29B.

The air velocity sensor 10B can be set in the extended supported state by stretching the dedicated air velocity sensor supporting device 29B, and a retracted supported state by contracting the dedicated air velocity sensor supporting device 29B in which state the air velocity sensor 10B is positioned closer to the moving frame 9 in the movement direction of the moving frame than in the extended supported state.

In other words, when the discharge velocity of the supplied air SA is to be tested, the air velocity sensor 10B in the extended supported state is automatically moved along a set serpentine route toward the other room wall 2D opposite from the room wall 2C provided with the frame-accommodating concavity 39 as shown in FIG. 5 for example. This is achieved by combining the movement of the moving frame 9 and the movement of the air velocity sensor 10B relative to the moving frame 9 in the longitudinal direction of the moving frame. This operation is accompanied by testing carried out by the air velocity sensor 10B in each position of the set route. Subsequent to the testing by the automatic movement of the air velocity sensor 10B along the set route, as shown in FIG. 11(a), the moving frame 9 is moved, to bring the distal end (alternatively, the air velocity sensor 10B) of the dedicated air velocity sensor supporting device 29B into contact with the room wall 2D on the side opposite from the room wall 2C provided with the frame-accommodating concavity 39. The moving frame 9 is further moved to the room wall 2D side, whereby the dedicated air velocity sensor supporting device 29B is contracted from a stretched state to a contracted state, and the supported state of the air velocity sensor 10B is switched from an extended supported state to a retracted supported state.

Subsequent to this switching, the moving frame 9 is moved to the vicinity of the room wall 2C provided with the frame-accommodating concavity 39. After being moved inside the room, the moving frame 9 is then extended and accommodated in the frame-accommodating concavity 39, as shown in FIG. 11(b). The air velocity sensor 10B in a retracted supported state is positioned in the wall-proximate area T quite close to the room wall 2C provided with the frame-accommodating concavity 39 (i.e., an area in which the air velocity sensor 10B could not be positioned if it remained in an extended supported state). The formation of curved streamline areas B1, B2 and eddy current areas A1, A2 can be eliminated by accommodating the moving frame 9 in the frame-accommodating concavity 39. In such a state, the air velocity sensor 10B is movably operated in the longitudinal direction of the moving frame so as to smoothly test the supplied air SA discharged in the wall-proximate area T without being affected by the curved streamline areas B1, B2 and the eddy current areas A1, A2.

The operation for switching the dedicated air velocity sensor supporting device 29B from a contracted state to a stretched state entails manually returning the air velocity sensor 10B from a retracted supported state to an extended supported state.

In the air velocity testing according to the present embodiment, the extended supported state of the air velocity sensor 10B acting as the filter test device 10 (see FIG. 9) is in a supported state in which the air velocity sensor 10B is positioned to one lateral side of the moving frame 9 at substantially the same height as the moving frame 9, as viewed in the longitudinal direction of the moving frame. For example, the distance d between the air velocity sensor 10B and the moving frame 9 in the movement direction of the moving frame is 200 mm, when the velocity v at which the supplied air SA is discharged from the lower surface 6a of the ceiling partition 6 is 0.3 to 0.6 m/s.

In the air velocity testing according to the present embodiment as described above, the distance h in the height direction between the air velocity sensor 10B and the lower surface 6a of the ceiling partition 6 is 150 mm.

Further Embodiments

The exit surfaces of the filter group G being tested are not limited to being formed in the ceiling surface of the room, and may also be formed in the side surfaces of the room. In such a case, the opposing room walls spanned by the moving frame 9 may be a combination of the ceiling and floor, or a combination of the opposing side walls.

The constituent material of the ceiling partition 6 is not limited to a perforated panel, and may be a net-shaped material or a sheet-shaped material.

In the above-described embodiment, the lower surface 6a of the ceiling partition 6 during air velocity testing and during normal service are used as the exit surfaces of the filter group G, and the moving frame 9 is disposed below the ceiling partition 6. Instead, the discharge surfaces 4a of the filters 4 disposed in the ceiling may also be used as the exit surfaces of the filter group G during air velocity testing and during normal service, and the moving frame 9 may be disposed below the filters 4, as shown in FIGS. 15 and 16. In this configuration, the supplied air SA discharged downward in parallel streams from the discharge surfaces 4a of the filters 4 can be tested.

In the above-described embodiment, the air velocity sensor 10B is set in a supported state positioned in the fringe part B1' of the curved streamline area B1 or in an external location C1' of the curved streamline area B1 in the vicinity of the fringe part, at substantially the same height as the moving frame 9, in order to set/mount the air velocity sensor 10B in an extended supported state on the moving frame 9. However, the height of the air velocity sensor 10B in the extended supported state is not limited to substantially the same height at the moving frame 9. Instead, the air velocity sensor 10B may be set in a supported state positioned in the fringe part B1' of the curved streamline area B1 or in an external location C1 of the curved streamline area B1 in the vicinity of the fringe part, at a position higher or lower than the moving frame 9, in order to set/mount the air velocity sensor 10B in an extended supported state on the moving frame 9.

In the above-described embodiment, a single moving frame 9 is disposed across the opposing room walls 2A and 2B, and the range in which the filter test device 10 can move is made to extend over all the exit surfaces of the filter group G by using the movement of the moving frame 9 and the movement of the filter test device 10, which is mounted on the moving frame 9, in the longitudinal direction of the moving frame. In lieu of this configuration, a plurality of moving frames 9 may be disposed in parallel, the range of movement of a plurality of filter test devices 10 can be made to extend over all the exit surfaces of the filter group G by using the movement of the moving frames 9 and the movement of the filter test devices 10, which is mounted on the moving frames 9, in the longitudinal direction of the moving frames.

In implementing the first aspect of the present invention described above, the movement range of the filter test device 10 is not necessarily required to extend over all the exit surfaces of the filter group G. In some cases, the movement range of the filter test device 10 may extend over only a portion of the exit surfaces of the filter group G.

When the moving frame 9 is moved by a drive mechanism, and the filter test device 10 is moved relative to the moving frame 9 by the drive mechanism, the mechanism is not limited to the timing belts described in the embodiment above, and various modes can be adopted. Also, the guide mechanism for guiding the movement of the moving frame 9, and the guide mechanism for guiding the movement of the filter test device 10 in relation to the moving frame 9 are not limited to the modes described in the embodiment above, and various other modes may also be adopted.

In the above-described embodiment, an interlocking shaft 26 causes two drive pulleys 25 to rotate in a synchronous manner to bring the movement speed of the two ends of the moving frame into conformity. In lieu of this configuration, it is also possible to use a drive structure that separately provides a motor for moving one end of the moving frame 9, and a motor for moving the other end of the moving frame 9, wherein the motors are caused to rotate in a synchronous manner to bring the movement speed of the two ends of the moving frame into conformity.

The cableveyor 37 described in the embodiment above is not the only possible cable-shaped component holding mechanism in which the cable-shaped components 18 and 19 extending from the filter test device 10 are held alongside the moving frame 9 while allowing the filter test device 10 to move in relation to the moving frame 9, or the only possible cable-shaped component holding mechanism in which the cable-shaped components 18 and 19 extended between the moving frame 9 and the room wall 2A are held along the room wall 2A while allowing the moving frame 9 to move. Various other modes may be adopted.

In the guide structure for bearing the two ends of the moving frame 9 in the longitudinal direction, by the moving device 23 that moves along the guide rails 22 using the guidance of the guide rails 22, an adapting mechanism allows the moving frame 9 and the moving device 23 to move relative to each other in the longitudinal direction of the moving frame, and the moving frame 9 and the moving device 23 to rotate relative to each other, on at least one of the two ends of the moving frame 9 in the longitudinal direction. In such a case, the specific structure of the adapting mechanism is not limited to a structure using a bearing 34 and rollers 35 as described in the embodiment above, and various other modes may be adopted. Also, the structure may be one in which only one movement is allowed; i.e., the relative movement of the moving frame 9 and the moving device 23 in the longitudinal direction of the moving frame between, or the relative rotation of the moving frame 9 and the moving device 23.

INDUSTRIAL APPLICABILITY

The filter test apparatus according to the present invention can be applied to clean booths used in rooms for manufacturing medicines and foodstuffs, as well as in rooms for manufacturing semiconductor components, and to various other clean rooms.

BRIEF DESCRIPTION OF THE DRAWINGS

FIG. 1 is a front view of a clean booth during leak testing of a filter;

FIG. 2 is a front view of the clean booth during discharge velocity testing of a filter;

FIG. 3 is a diagram showing a scanning pattern of a downstream suction device;

FIG. 4 is a front view of the clean booth during normal service;

FIG. 5 is a diagram showing the exhaust structure of a guide concavity and a frame-accommodating concavity;

FIG. 6 is a cross-sectional front view of a supplied air chamber showing an arrangement of an upstream suction device;

FIG. 7 is a perspective view showing the structure of a support device for the downstream suction device;

FIG. 8 is a side view showing the distribution of an eddy current and a curved streamline area;

FIG. 9 is a side view showing the structure of a support device for an air discharge velocity sensor;

FIG. 10 is a diagram showing a scanning pattern of the air discharge velocity sensor;

FIG. 11 is a side view showing the manner in which a switch is made to the retraction support state of the support device for the discharge velocity sensor;

FIG. 12 is a block diagram of a powder mixing apparatus;

FIG. 13 is an exploded perspective view showing a movement structure;

FIG. 14 is a cross-sectional view showing the movement structure;

FIG. 15 is a layout drawing of a moving frame showing another embodiment; and

FIG. 16 is a layout drawing of a moving frame showing another embodiment.

DESCRIPTION OF REFERENCE NUMERALS AND SIGNS 2 clean room
2A room wall
2B room wall
2C room wall
2D room wall
4 filter
5 supplied air chamber
6 ceiling partition
6a lower surface
8 circulation channel
9 moving frame, support state switching means
10 filter test device
11 mixing means
11A first air supply means, second air supply means
11B production means
11C diluting means
11D dispersion means
11E collision member
12 upstream suction device
15 setting means, scanning control means, suction device switching means
18 cable-shaped component
19 cable-shaped component
20 downstream measurement means
21 upstream measurement means
22 guide mechanism
23 guide mechanism
23 drive mechanism
24 drive mechanism
25 drive mechanism
26 drive mechanism
27 drive mechanism
29 support state switching means, support device
31 drive mechanism
32 drive mechanism
33 drive mechanism
34 adapting mechanism
35 adapting mechanism
36 adapting mechanism
37A cable-shaped component holding mechanism
37B cable-shaped component holding mechanism
38 guide concavity
39 frame-accommodating concavity
40 cover
41 cover
43 suction means
B1 curved streamline area
B2 curved streamline area
B1' fringe part of the curved streamline area
C1' external location of the curved streamline area in the vicinity of the fringe part of the curved streamline area
CA production gas
DA diluting gas
d distance between the filter test device and the moving frame in the movement direction of the moving frame
h distance between the filter test device and the exit surface of the filter group in the height direction
F2 suction means
G filter group
P powder
SA supplied air
V1 production flow rate adjustment valve
V2 diluting flow rate adjustment valve
X nozzle

The invention claimed is:

1. A filter testing apparatus adapted for use in a clean room provided with filters for purifying air supplied to the room, a ceiling surface of the room acting as exit surfaces of the filters, the apparatus comprising:

a moving frame oriented along the exit surfaces so as to be movable in a direction along the exit surfaces orthogonal to a longitudinal direction of the moving frame, and spanned between two opposing side walls in the room at a position near the exit surfaces; and a filter test device for measuring velocity of air discharged from the exit surfaces is mounted on the moving frame to be movable along the longitudinal direction of the moving frame through a supporting device;

wherein the supporting device supports the filter test device with the filter test device positioned to one lateral side of the moving frame and projected at substantially the same height as the moving frame from the moving frame as viewed in the longitudinal direction of the moving frame, and wherein the filter test device can change a supported state thereof between a retracted supported state in which the filter test device is proximate to the moving frame at substantially the same height as the moving frame in the movement direction of the moving frame, and an extended supported state in which the filter test device is set at a distance away from the moving frame at substantially the same height as the moving frame in the movement direction of the moving frame.

2. A filter testing apparatus according to claim 1, wherein the supporting device can stretch and contract in the movement direction of the moving frame, to be in the extended supported state when stretched, and to be in the retracted supported state when contracted.

3. A filter testing apparatus according to claim 1, wherein a moving frame-accommodating concavity is defined in one of the side walls positioned at the ends of the moving frame in its moving direction; and the supporting device supports the filter test device with the filter test device projected to the side opposite from the concavity.

4. A filter testing apparatus according to claim 1, wherein a distance between the moving frame and the filter test device is 75 mm to 250 mm when the filter test device is in the extended supported state.

5. A filter testing apparatus according to claim 1, wherein a distance between the exit surfaces and the filter test device in a vertical direction is 100 mm or more.

6. A method for operating a filter testing apparatus adapted for use in a clean room provided with filters for purifying air supplied to the room, a ceiling surface of the room acting as exit surfaces of the filters, the method comprising the steps of:

providing a filter testing apparatus comprising:
a moving frame oriented along the exit surfaces so as to be movable in a direction along the exit surfaces orthogonal to a longitudinal direction of the moving frame, and spanned between two opposing side walls in the room at a position near the exit surfaces, a moving frame-accommodating concavity being disposed in one of the side walls positioned at opposing ends of a moving direction of the moving frame; and a filter test device for measuring velocity of air discharged from the exit surfaces is mounted on the moving frame through a supporting device to be movable along the longitudinal direction of the moving frame;

wherein the supporting device supports the filter test device with the filter test device projected at substantially the same height as the moving frame in a direction substantially orthogonal to the moving frame and to the side opposite from the moving frame-accommodating concavity as viewed in the longitudinal direction of the moving frame; and wherein the filter test device can change a supported state thereof between a retracted supported state in which the filter test device is proximate to the moving frame, and an extended supported state in which the filter test device is set at a distance away from the moving frame;

measuring, with the filter test device in the extended supported state, the air velocity in areas other than the wall adjacent area that is proximate to the side wall provided with the moving frame-accommodating concavity; and measuring, with the filter test device in the retracted supported state, the air velocity in the wall adjacent area that is proximate to the side wall provided with the moving frame-accommodating concavity.

7. A method for operating a filter testing apparatus according to claim 6, further comprising the steps of causing the moving frame to move to the side wall opposite from the side wall provided with the moving frame-accommodating concavity, bringing the supporting device into contact with the opposite side wall, and changing the filter test device from the extended supported state to the retracted supported state.

8. A method for operating a filter testing apparatus according to claim 6, wherein the step for measuring the air velocity in the wall adjacent area comprises the steps of:

accommodating the moving frame in the moving frame-accommodating concavity, and positioning the filter test device in the retracted supported state in the wall adjacent area; and causing the filter test device in the retracted supported state to move along the longitudinal direction of the moving frame with the moving frame being accommodated in the concavity.

* * * * *